(12) United States Patent
Huentelman

(10) Patent No.: US 11,926,873 B2
(45) Date of Patent: Mar. 12, 2024

(54) METHODS FOR PREDICTING ONSET OF A MIGRAINE IN A SUBJECT BY DETECTING STXBP3 RNA LEVELS

(71) Applicant: THE TRANSLATIONAL GENOMICS RESEARCH INSTITUTE, Phoenix, AZ (US)

(72) Inventor: Matthew Huentelman, Phoenix, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 52 days.

(21) Appl. No.: 17/127,967

(22) Filed: Dec. 18, 2020

(65) Prior Publication Data
US 2021/0115514 A1    Apr. 22, 2021

Related U.S. Application Data

(62) Division of application No. 15/736,296, filed as application No. PCT/US2016/038243 on Jun. 17, 2016, now Pat. No. 10,889,861.

(60) Provisional application No. 62/181,041, filed on Jun. 17, 2015.

(51) Int. Cl.
| | |
|---|---|
| *C12Q 1/6883* | (2018.01) |
| *C12Q 1/6809* | (2018.01) |
| *C12Q 1/6876* | (2018.01) |
| *C12Q 1/6869* | (2018.01) |
| *C12Q 1/6879* | (2018.01) |

(52) U.S. Cl.
CPC ......... *C12Q 1/6883* (2013.01); *C12Q 1/6809* (2013.01); *C12Q 1/6876* (2013.01); *C12Q 1/6869* (2013.01); *C12Q 1/6879* (2013.01); *C12Q 2600/118* (2013.01); *C12Q 2600/124* (2013.01); *C12Q 2600/158* (2013.01); *C12Q 2600/16* (2013.01); *C12Q 2600/166* (2013.01); *G01N 2800/2807* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,210,891 B1 | 4/2001 | Nyren et al. | |
| 6,258,568 B1 | 7/2001 | Nyren | |
| 6,274,320 B1 | 8/2001 | Rothberg et al. | |
| 7,057,026 B2 | 6/2006 | Barnes et al. | |
| 7,414,116 B2 | 8/2008 | Milton et al. | |
| 7,427,673 B2 | 9/2008 | Balasubramanian et al. | |
| 2009/0026082 A1 | 1/2009 | Rothberg et al. | |
| 2009/0127589 A1 | 5/2009 | Rothberg et al. | |
| 2010/0035252 A1 | 2/2010 | Rothberg et al. | |
| 2010/0123143 A1 | 5/2010 | Chang | |
| 2010/0153018 A1* | 6/2010 | Bussemaker | G16B 20/20 702/19 |
| 2010/0188073 A1 | 7/2010 | Rothberg et al. | |
| 2010/0197507 A1 | 8/2010 | Rothberg et al. | |
| 2010/0282617 A1 | 11/2010 | Rothberg et al. | |
| 2010/0300559 A1 | 12/2010 | Schultz et al. | |
| 2010/0300895 A1 | 12/2010 | Nobile et al. | |
| 2010/0301398 A1 | 12/2010 | Rothberg et al. | |
| 2010/0304982 A1 | 12/2010 | Hinz et al. | |
| 2012/0225798 A1 | 9/2012 | Cantor et al. | |
| 2013/0165336 A1 | 6/2013 | Liew et al. | |
| 2013/0203320 A1 | 8/2013 | Ghalambor | |
| 2013/0252835 A1* | 9/2013 | Koh | G16B 50/00 435/6.12 |
| 2013/0280725 A1* | 10/2013 | Ismagilov | B01L 3/50273 435/6.12 |
| 2013/0295572 A1 | 11/2013 | Liu et al. | |
| 2014/0004526 A1* | 1/2014 | Dauner | C12Y 101/01047 435/252.32 |
| 2014/0243212 A1* | 8/2014 | Lo | G16B 30/10 702/19 |
| 2015/0197809 A1 | 7/2015 | Myers et al. | |

FOREIGN PATENT DOCUMENTS

| | | |
|---|---|---|
| WO | 1991006678 A1 | 5/1991 |
| WO | 2007123744 A2 | 11/2007 |

OTHER PUBLICATIONS

Bischoff et al Reproductive BioMedicine Online. Feb. 2003. 6(3): 349-351 (Year: 2003).*
Jones et al Malar J. 2012. 11:266, p. 1-10 (Year: 2012).*
Min et al BMC Genomics. 2010. 11:96 (Year: 2010).*
Palmer BMC Genomics. 2006. 7:115 (Year: 2006).*
Hanke et al. Clinical Chemistry. 2007. 53: 2070-2077 (Year: 2007).*
Wilson et al Blood. 2006. 108: 685-696 (Year: 2006).*
Zhao et al Cephalalgia. Published online Dec. 2015.36(7): 648-657 and Supplementary Tables S1-S4 (Year: 2015).*
Bischoff, F. Z., et al. Detecting fetal DNA from dried maternal blood spots: another step towards broad scale non-invasive prenatal genetic screening and feasible testing. Reproductive BioMedicine Online 2003; 6(3):349-351.
Mersy, E., et al. Cell-Free RNA Is a Reliable Fetoplacental Marker in Noninvasive Fetal Sex Determination. Clinical Chemistry 2015; 61(12):1515-1523.
Plantier, J-C., et al. HIV-1 resistance genotyping on dried serum spots. AIDS 2005; 19(4):391-397.

(Continued)

*Primary Examiner* — Carla J Myers
(74) *Attorney, Agent, or Firm* — Rodney J. Fuller; BOOTH UDALL FULLER, PLC

(57) ABSTRACT

The present invention relates to a method of creating a biomarker profile, the method comprising the steps of: obtaining a sample of biofluid from a subject, wherein the sample is stored on a sample collection apparatus; removing the sample from the sample collection apparatus; extracting nucleic acids from the sample; sequencing the extracted nucleic acids to generate sequence data; and analyzing the sequence data using a two-step analytical methodology to create the biomarker profile. The present invention is also directed to methods of determining the sex of an in utero fetus, predicting onset of a migraine in a subject, and of tracking athletic performance in a subject.

18 Claims, 19 Drawing Sheets

(56) References Cited

OTHER PUBLICATIONS

Rath, B. A., et al. Antiviral Resistance and Correlates of Virologic Failure in the first Cohort of HIV-Infected Children Gaining Access to Structured Antiretroviral Therapy in Lima, Peru: A Cross-Sectional Analysis. BMC Infectious Diseases 2013; 13:1.
Hollegaard, M. V., et al. Archived neonatal dried blood spot samples can be used for accurate whole genome and exome-targeted next-generation sequencing. Molecular Genetics and Metabolism 2013; 110(1-2):65-72.
Aberg, K. A., et al. High quality methylome-wide investigations through next-generation sequencing of DNA from a single archived dry blood spot. Epigenetics 2013; 8(5):542-547.
Hart, S. N., et al. Calculating Sample Size Estimates for RNA Sequencing Data. Journal of Computational Biology 2013; 20(12):970-978.
Baudhuin, L. M. Quality guidelines for next-generation sequencing. Clin Chem 2013; 59:858-859.
Castel, S. E., et al. RNA interference in the nucleus: roles for small RNAs in transcription, epigenetics and beyond. Nat Rev Genet 2013; 14(2):100-112.
Fire, A., et al. Potent and specific genetic interference by double-stranded RNA in Caenorhabditis Elegans. Nature 1998; 391(6669):806-811.
Lee, Y. S., et al. MicroRNAs in cancer. Annu Rev Pathol 2009; 4:199-227.
Ross, J. S., et al. miRNA: the new gene silencer. Am J Clin Pathol 2007; 128(5):830-836.
Ying, S-Y., et al. The MicroRNA (miRNA): Overview of the RNA Genes that Modulate Gene Function. Mol Biotechnol 2008; 38(3):257-268.
Ronaghi, M., et al. Real-time DNA sequencing using detection of pyrophosphate release. Analytical Biochemistry 1996; 242(1):84-89.
Ronaghi, M. Pyrosequencing sheds light on DNA sequencing. Genome Res 2001; 11(1):3-11.
Ronaghi, M., et al. A sequencing method based on real-time pyrophosphate. Science 1998; 281(5375):363-365.
Rusk, N. Torrents of Sequence. Nat Meth 2011; 8(1):44.
Pennisi, E. Semiconductors inspire new sequencing technologies. Science 2010; 327(5970):1190.
Perkel, J. Making contact with sequencing's fourth generation. Biotechniques 2011; 50(2):93-95.
Zhao, S., et al. Comparison of RAN-Seq and Microarray in Transcriptome Profiling of Activated T Cells. PLoS ONE 2014; 9(1):e78644.
Hrdlickova, R., et al. RNA-Seq Methods for Transcriptome Analysis. Wiley Interdiscip Rev RNA 2017; 8 (1):10.1002/wrna.1364.
Jones, L. J., et al. RNA quantitation by fluorescence-based solution assay: RiboGreen reagent characterization. Anal Biochem 1998; 265:368-374.
Wan, E., et al. Green Technologies for Room Temperature Nucleic Acid Storage. Current Issues Molecular Biology 2010; 12(3):135-142.

\* cited by examiner

METHODS FOR PREDICTING ONSET OF A MIGRAINE IN A SUBJECT BY DETECTING STXBP3 RNA LEVELS

CROSS REFERENCE TO RELATED APPLICATIONS

This application is a divisional of U.S. patent application Ser. No. 15/736,296, filed Dec. 13, 2017 (published as US20180187260), which is the U.S. National Stage of International Application No. PCT/US2016/038243, filed Jun. 17, 2016, which claims priority to U.S. Provisional Application No. 62/181,041 filed Jun. 17, 2015, the contents of each of which are incorporated herein by reference in their entireties.

TECHNICAL FIELD

This application generally relates to systems and methods for obtaining biological molecules usable in downstream applications from a sample, and more specifically relates to systems and methods of extracting nucleic acids from a dried biological sample for downstream analyses, including sequencing analyses.

BACKGROUND

Preserving the structural and functional integrity of biological molecules or biomolecules during extraction, storage, isolation, and/or purification from a biological sample is essential for various downstream applications/analyses. For example, some of these downstream applications/analyses may include analyte detection, sensing, forensic, diagnostic, prognostic, theranostic, and/or therapeutic applications, sequencing, amplification, among other potential uses for these biomolecules. The ultimate success of these downstream applications may depend on maintaining the integral structure and function of the target biomolecules. For example, various factors, such as temperature, humidity, pH, chemical or enzymatic-mediated degradation, or the presence of contaminants may cause degradation of the biomolecules.

RNA is one of the most unstable biomolecules due to chemical self-hydrolysis and enzyme-mediated degradation. The storage, extraction, and stabilization of RNA derived from a biological sample is sensitive to a number of environmental factors including, but not limited to, the substance on or in which the sample is stored, the buffer used to extract or collect the RNA, solution pH, temperature, and the presence of ribonucleases. RNA is typically stored under refrigeration (e.g., 4° C.--80° C.) in both purified and unpurified forms to prevent hydrolysis and enzymatic degradation and to preserve the integrity of the RNA sample. As such, it would desirable to develop a methodology in which a sample can be obtained and stored at ambient temperatures and then the RNA and other biomolecules can then be extracted.

Moreover, scientists looking to perform next-generation sequencing (NGS) must consider the manner and method of sample preparation. The way that DNA or RNA is isolated from a sample and subsequently stored, the preparation chosen to construct sequencing libraries, and the type of sequencing that is being performed, all become crucial factors in the experimental design (Baudhuin L. M. (2013) Quality guidelines for next-generation sequencing. Clin Chem 59 858-859).

For RNA sequencing in particular, classes of molecules are, at least in part, defined and sequenced by their size. MicroRNAs (miRNAs; 16-27 nucleotides (nt)), small interfering RNAs (siRNAs; 16-27 nt), and PIWI interacting RNAs (piRNA; ~30 nt) are all part of a class of small non-coding RNA involved in sequence-specific gene silencing (Castel S. E., Martienssen, R. A. (2013) RNA interference in the nucleus: roles for small RNAs in transcription, epigenetics and beyond. Nat 14, 100-112). While currently known as the smallest functional class, the depth of small RNA's biological significance to regulate gene expression is still being uncovered some 15 years after discovery (Fire A., Xu S., Montgomery M. K., Kostas, et al. (1998) Potent and specific genetic interference by double-stranded RNA in *Caenorhabditis Elegans*. Nature 391, 806-811.)

Until recently, methods for isolating RNA from tissues of origin had been thought to recover all RNA species. Roughly from large to small, RNA as a family of molecules includes coding RNA (mRNA), long noncoding RNA (lncRNA), transfer RNA (tRNA), small nucleolar RNA (snoRNA), PIWI Interacting RNA (piRNA), and miRNA (Castel S. E., Martienssen, R. A. (2013) RNA interference in the nucleus: roles for small RNAs in transcription, epigenetics and beyond. Nat 14, 100-112.) The purification of all species of RNA is implied in the description of many commercially available kits and methods touting "total" RNA isolation. In fact, it had been used for methods that do not recover small RNA at all, such as column-based kits that washed the small RNA off the column during the cleaning steps. In addition, other kits used ratios of salt and alcohol that are too low to precipitate small RNA out of solution. There are now many commercially available kits for small RNA purification from which to choose. Systematic testing shows that the performance of RNA extraction kits varies quite a bit depending on the type of sample. Reasonably, different kits may deal with a particular sample type better than another. For example, a fibrous tissue such as muscle has to be handled differently than lipid-rich nervous tissue. When available, the best option may be to choose a kit specifically designed to deal with the challenges of a particular type of tissue. There is a need to identify methods to maximize the amount of RNA extracted from biological samples with any given extraction kit especially when the material is limited.

The discovery and reliable detection of markers for any type of disease or condition may be complicated by the relative inaccessibility of some forms of tissue (e.g., central nervous system tissue) or an inability to biopsy or test tissue. RNAs derived from hard to access tissues, such as neurons within the brain and spinal cord, have the potential to get to the periphery where they can be detected non-invasively. The formation and release of extracellular microvesicles and RNA binding proteins have been found to carry RNA from cells to the periphery and protect the RNA from degradation. Extracellular miRNAs detectable in peripheral circulation can provide information about cellular changes associated with human health and disease. In order to associate miRNA signals present in cell-free peripheral biofluids, there is a need to develop systems and methodology for obtaining, storing, extracting, and performing downstream analyses on these biofluids.

The ability to meaningfully profile peripheral biofluids to monitor and gain insights about the underlying conditions and diseases would bring significant benefits to monitoring disease progression and treatment efficacy. Development of diagnostic tests and preventative and treatment therapies for diseases and conditions of medical concern is encumbered by the complexity of pathomechanisms some of these diseases and conditions, as well as the difficulty of achieving an accurate diagnosis in early, asymptomatic stages of diseases and conditions.

As such, there is great interest in the identification of biomarkers in the blood and other biofluids. However, due to the concerns regarding sampling from CSF (e.g., extensive numbers of punctures of the spinal column), large volumes of urine needed for biomarker extraction, and difficult collection regimens with which patients may have to comply (e.g., saliva collection), there is a need to provide a simple and easily usable methodology for the ready collection of biofluids and downstream isolation and processing.

The articles, treatises, patents, references, and published patent applications described above and herein are hereby incorporated by reference in their entirety for all purposes.

SUMMARY

The present invention is directed to a method of creating a biomarker profile, the method comprising the steps of: obtaining a sample of biofluid from a subject, wherein the sample is stored on a sample collection apparatus; removing the sample from the sample collection apparatus; extracting nucleic acids from the sample; sequencing the extracted nucleic acids to generate sequence data; and analyzing the sequence data using a two-step analytical methodology to create the biomarker profile.

In some aspects, the biofluid is selected from the group consisting of blood, plasma, serum, urine, sputum, cerebrospinal fluid, milk, and ductal fluid. In one embodiment, the biofluid is a single drop of blood.

In other aspects, the sample collection apparatus comprises cellulose paper on which the biofluid is placed to dry. In one aspect, the cellulose paper has not been treated with any chemical stabilizers of nucleic acids.

In various embodiments, the nucleic acids are RNA. In a particular embodiment, the RNA is extracellular RNA.

In certain embodiments, the two-step analytical methodology comprises: a) determining i) and ii) as: i) the coefficient of variance for an RNA transcript in the sample; and ii) the coefficient of variance of the RNA transcript in a reference sample; and b) removing the RNA transcript from the biomarker profile if i) is greater than ii). In one aspect, the reference sample is not allowed to dry prior to extracting nucleic acids.

In yet other aspects, the sample is obtained from the subject through a non-invasive methodology such as a finger prick.

The present invention also relates to a method of determining the sex of an in utero fetus, the method comprising the steps of: obtaining a sample of biofluid from a pregnant mother, wherein the sample is stored on a sample collection apparatus; removing the sample from the sample collection apparatus; extracting nucleic acids from the sample; sequencing the extracted nucleic acids to generate sequence data; and analyzing the sequence data to determine the sex of the in utero fetus, wherein the in utero fetus is male if expression of Y chromosome nucleic acids is similar to or greater than expression of X chromosome nucleic acids in the sample. In certain aspects, the nucleic acids are extracellular nucleic acids.

The present invention is also directed to a method of predicting onset of a migraine in a subject, the method comprising the steps of: obtaining a set of samples of biofluid from the subject collected over time intervals and stored on sample collection apparatuses; removing the set of samples from the sample collection apparatuses; extracting nucleic acids from the set of samples; sequencing the extracted nucleic acids to generate sequence data; and analyzing the sequence data to identify sudden increases in gene expression of ATP binding cassette subfamily C member 1 (ABCC1) and/or syntaxin binding protein 3 (STXBP3), wherein a sudden increase in expression of ABCC1 and/or STXBP3 indicates onset of a migraine in the subject.

In certain aspects, a sudden increase in expression is an increase of at least 5 times, at least 10 times, at least 15 times, at least 20 times, or at least 30 times in a 6-hour period, in a 12-hour period, or a 24-hour period.

In other aspects, the time intervals are 1 hour, 2 hours, 3 hours, 4 hours, 5 hours, 6 hours, 8 hours, 10 hours, 12 hours or 24 hours.

In some aspects, the set of samples is a set of single drops of blood allowed to dry on the sample collection apparatuses.

In one embodiment, the method further comprises treating the subject for migraine, wherein treating the migraine comprises administering to the subject an effective amount of a non-steroidal anti-inflammatory drug (NSAID), a triptan, an ergotamine, metoclopramide, lidocaine or a combination thereof. Treatment may be initiated just prior to onset of the migraine.

In yet other aspects, the present invention relates to a method of tracking athletic performance in a subject, the method comprising the steps of: obtaining a set of samples of biofluid from the subject collected before, during, and after aerobic exercise and stored on sample collection apparatuses; removing the set of samples from the sample collection apparatuses; extracting nucleic acids from the set of samples; sequencing the extracted nucleic acids to generate sequence data; and analyzing the sequence data to identify increases in gene expression of dysferlin (DYSF) and/or matrix metallopeptidase 9 (MMP9), wherein an increase in expression of DYSF and/or MMP9 compared to a reference indicates improved athletic performance in the subject.

In one aspect, the reference is a measurement of expression of DYSF and/or MMP9 in a set of samples from the subject determined from an earlier time point in the athletic training of the subject.

In certain aspects, improved athletic performance is indicated by increased endurance, greater muscle strength or a combination thereof.

DETAILED DESCRIPTION

Figure 1:
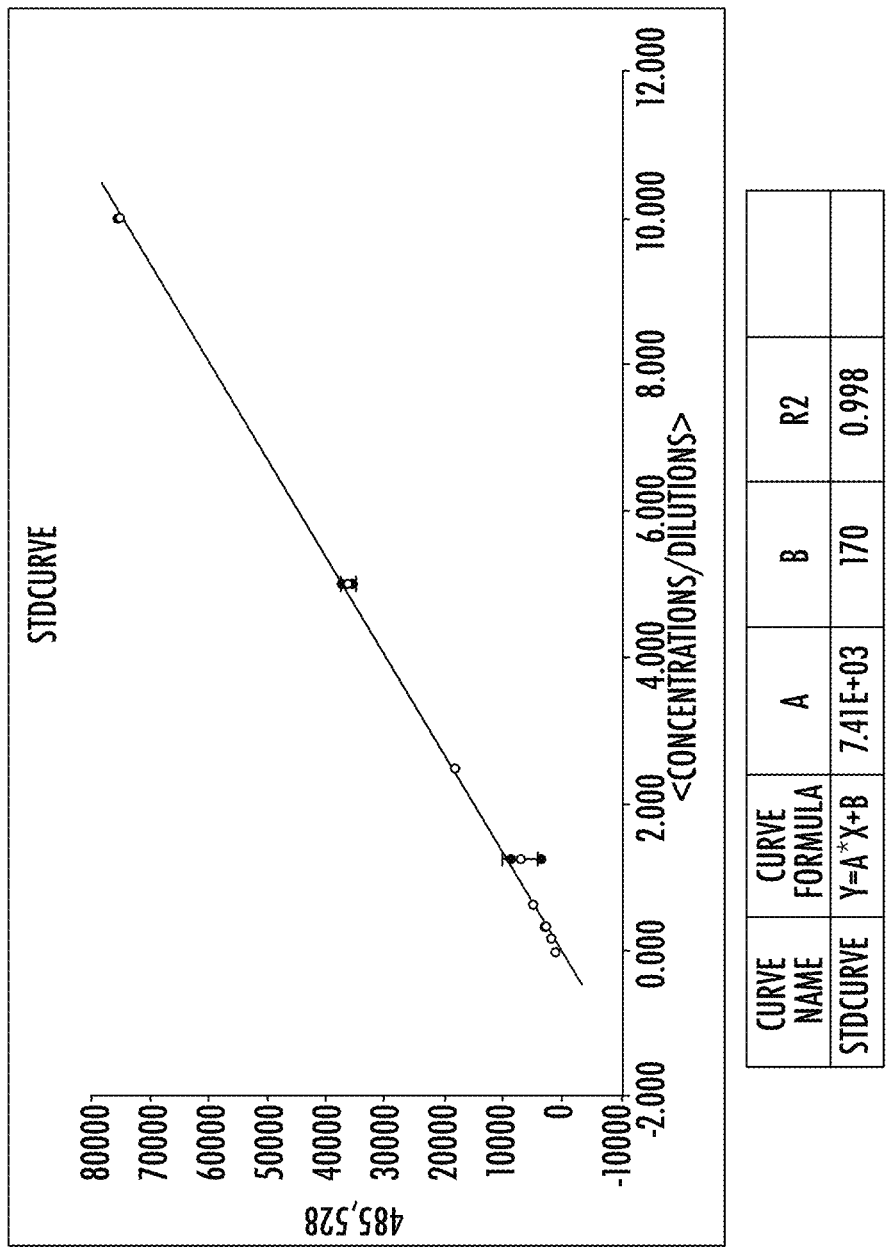
FIG. 1 depicts the standard curve used to calculate the RNA total yields in Table 1.

Some embodiments of the invention provide methods for obtaining, storing, isolating, extracting, and/or analyzing one or more biomolecules from a sample. For example, some embodiments of the invention can be intended to be used subjects to regularly obtain samples from the subjects on a regular or irregular/frequent or infrequent basis. In some aspects, embodiments of the instant invention can be used to obtain samples from the subjects in relatively small volumes or other quantities at regular intervals. By way of example only, some aspects of the invention can be employed in obtaining, storing, isolating, extracting, and/or analyzing biomolecules in a small volume of biofluid (e.g., drop-like quantities of blood, plasma, serum, cerebrospinal fluid, urine, saliva, etc.). Moreover, in some embodiments, the methodologies of the instant invention can be used in conjunction with the small quantity of biofluid to obtain multiple samples from a single subject, potentially over an extended period of time (e.g., longitudinal samples from one or more subjects). In other words, due to the relatively small quantities required for use with the instant methodologies, the subjects may be able to obtain samples for downstream analyses on a regular basis (e.g., minutes, hours, days, weeks, months, years, etc.).

In some embodiments, the methodology of the instant invention can be used in conjunction with the identification/analysis of one or more markers of one or more diseases, conditions, medical states, etc. For example, in some embodiments, methodologies of the invention can be used to identify and/or analyze one or more biomarkers associated with a disease, condition, and/or medical state using a sample of relatively small quantities. As such, embodiments of the invention can be employed in medically related analyses to diagnose, assess, provide prognostic information, and make therapeutic decisions regarding any biologically related state. In other words, any state of the subject may be assessed using some embodiments of the invention.

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one."

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some embodiments, the subject is a mammal. In other embodiments, the subject is a human.

As used herein the term "diagnosing" or "diagnosis" refers to the process of identifying a medical condition or disease by its signs, symptoms, and in particular from the results of various diagnostic procedures, including e.g. detecting the expression of the nucleic acids according to at least some embodiments of the invention in a biological sample obtained from an individual. Furthermore, as used herein the term "diagnosing" or "diagnosis" encompasses screening for a disease, screening for the presence and/or absence of a condition, such as a medical condition, detecting a presence or a severity of a disease, distinguishing a disease from other diseases including those diseases that may feature one or more similar or identical symptoms, providing prognosis of a disease, monitoring disease progression or relapse, as well as assessment of treatment efficacy and/or relapse of a disease, disorder or condition, as well as selecting a therapy and/or a treatment for a disease, optimization of a given therapy for a disease, monitoring the treatment of a disease, and/or predicting the suitability of a therapy for specific patients or subpopulations or determining the appropriate dosing of a therapeutic product in patients or subpopulations. The diagnostic procedure can be performed in vivo or in vitro. In some embodiments, the methodologies according to the invention can be used in diagnosing diseases, conditions, etc. using samples of relatively small volumes of biofluids, such as one or more drops of blood.

"Detection" as used herein refers to detecting the presence of a component (e.g., a nucleic acid sequence) in a sample. Detection also means detecting the absence of a component. Detection also means measuring the level of a component, either quantitatively or qualitatively. With respect to the method of the invention, detection also means identifying or diagnosing one or more conditions or stages/likely successful therapeutic solutions in a subject. "Early detection" as used herein refers to identifying or diagnosing conditions or diseases in a subject at an early stage of the disease or condition (e.g., before there are any detectable/noticeable symptoms).

"Differential expression" as used herein refers to qualitative or quantitative differences in the temporal and/or cellular expression patterns of an RNA transcript and/or translated peptide/protein within and among cells and tissue. For example, differentially expressed transcripts can qualitatively have its expression altered, including an activation or inactivation, in, e.g., normal versus disease/altered state/condition tissue. Genes, for instance, may be turned on or turned off in a particular state, relative to another state thus permitting comparison of two or more states. A qualitatively regulated gene or transcript may exhibit an expression pattern within a state or cell type that may be detectable by standard techniques. Some transcripts will be expressed in one state or cell type, but not in both. Alternatively, the difference in expression may be quantitative, e.g., in that expression is modulated, up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, northern analysis, whole transcriptome/RNA sequencing, RNase protection, and any other methods now known or developed in the future.

In some embodiments, the term "level" refers to the expression level of a nucleic acid according to at least some embodiments of the present invention. Typically, the level of the nucleic acid in a biological sample obtained from the subject is different (e.g., increased or decreased) from the level of the same nucleic acid in a similar sample obtained from a healthy individual (examples of biological samples are described herein). Alternatively, the level of the nucleic acid in a biological sample obtained from the subject is different (e.g., increased) from the level of the same nucleic acid in a similar sample obtained from the same subject at an earlier time point. Alternatively, the level of the nucleic acid in a biological sample obtained from the subject is different (e.g., increased) from the level of the same nucleic acid in a non-diseased tissue obtained from said subject. Typically, the expression levels of the nucleic acid of the invention are independently compared to their respective control level.

The term "expression level" is used broadly to include a genomic expression profile, e.g., an expression profile of nucleic acids. Profiles may be generated by any convenient means for determining a level of a nucleic acid sequence e.g. quantitative hybridization of nucleic acid, labeled nucleic acid, amplified nucleic acid, cDNA, etc., quantitative PCR, ELISA for quantitation, sequencing (e.g., RNA sequencing) and the like, and allow the analysis of differential gene expression between two samples. A subject or sample, e.g., cells or collections thereof (e.g., tissues, fluids, etc.) is assayed. Samples are collected by any convenient method, as known in the art. According to some embodiments, the term "expression level" means measuring the abundance of the nucleic acid in the measured samples.

Expression level or other determinable traits regarding nucleic acids may function as one or more markers. As described herein, the markers are preferably then correlated with the presence or stage of a disease, condition, or medical state. For example, such correlating may optionally comprise determining the concentration of each of the plurality of markers, and individually comparing each marker concentration (e.g., expression level) to a threshold level. Optionally, if the marker concentration is above the threshold level, the marker concentration correlates with diseases, conditions and possibly stages thereof. Optionally, a plurality of marker concentrations correlates with neurological conditions and stages/treatments thereof. Alternatively, such correlating may optionally comprise determining the concentration of each of the plurality of markers, calculating a single index value based on the concentration of each of the plurality of markers, and comparing the index value to a threshold level. Also alternatively, such correlating may optionally comprise determining a temporal change in at least one of the markers, and wherein the temporal change is used in the correlating step.

A marker panel may be analyzed in a number of fashions well known to those of skill in the art. For example, each member of a panel may be compared to a "normal" value, or a value indicating a particular outcome. A particular diagnosis/prognosis may depend upon the comparison of each marker to this value; alternatively, if only a subset of markers is outside of a normal range, this subset may be indicative of a particular diagnosis/prognosis. The skilled artisan will also understand that diagnostic markers, differential diagnostic markers, prognostic markers, time of onset markers, disease or condition differentiating markers, etc., may be combined in a single assay or device. Markers may also be commonly used for multiple purposes by, for example, applying a different threshold or a different weighting factor to the marker for the different purpose(s).

In the methods of the invention, a "significant elevation" in expression levels of the plurality of markers/nucleic acids refers, in different embodiments, to a statistically significant elevation, or in other embodiments to a significant elevation as recognized by a skilled artisan. In additional embodiments, a significant elevation refers to an increase in the expression of a plurality of markers/nucleic acids.

The term "about" as used herein refers to +/−10%.

Diagnostic methods differ in their sensitivity and specificity. The "sensitivity" of a diagnostic assay is the percentage of diseased individuals who test positive (percent of "true positives"). Diseased individuals not detected by the assay are "false negatives". Subjects who are not diseased and who test negative in the assay are termed "true negatives". The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

Diagnosis of a disease, condition, or medical state according to at least some embodiments of the present invention can be affected by determining a level of a polynucleotide according to at least some embodiments of the present invention in a biological sample obtained from the subject, wherein the level determined can be correlated with predisposition to, or presence or absence of the disease.

The term "sample" or "biological sample" as used herein means a sample of biological tissue or fluid/biofluid or an excretion sample that may comprise biological molecules, such as nucleic acids. Such samples include, but are not limited to, tissue or fluid isolated from subjects. Biological samples may also include sections of tissues such as biopsy and autopsy samples, frozen sections, blood, plasma, serum (SER), sputum, stool and mucus from a living or deceased subject. In some specific embodiments, the sample may comprise a small volume of a biofluid, such as blood. For example, in some aspects, the sample may comprise one or more drops of blood that have been obtained from a finger puncture of the subject. Biological sample also refers to organs such as liver, lung, and peritoneum. Biological samples also include explants and primary and/or transformed cell cultures derived from animal or patient tissues. Biological samples may also be blood, a blood fraction, gastrointestinal secretions, or tissue sample. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

In some embodiments the sample obtained from the subject is a body fluid or excretion sample including but not limited to seminal plasma, blood, SER, urine, prostatic fluid, seminal fluid, semen, the external secretions of the skin, respiratory, intestinal, and genitourinary tracts, tears, CSF, sputum, saliva, milk, peritoneal fluid, pleural fluid, peritoneal fluid, cyst fluid, lavage of body cavities, broncho alveolar lavage, lavage of the reproductive system and/or lavage of any other organ of the body or system in the body, and stool.

Numerous well known tissue or fluid collection methods can be utilized to collect the biological sample from the subject in order to determine the expression level of the biomarkers of the invention in said sample of said subject.

Examples include, but are not limited to, blood sampling, urine sampling, stool sampling, sputum sampling, aspiration of pleural or peritoneal fluids, fine needle biopsy, needle biopsy, core needle biopsy and surgical biopsy, and lavage. Regardless of the procedure employed, once a biopsy/sample is obtained the level of the markers/nucleic acids can be determined and a diagnosis can thus be made.

In some embodiments, the sample can be collected and/or stored using a sample collection apparatus. In some embodiments, the sample collection apparatus can be configured and arranged to receive a liquid biofluid and to enable storage of that liquid biofluid at ambient and/or refrigerated temperatures. For example, in some aspects, the sample collection apparatus can be configured to receive the biofluid such that the biofluid can be absorbed into/within the structure of the apparatus for drying purposes. Moreover, in some aspects, the sample collection apparatus can be configured to provide a relatively nuclease-free environment for the biofluid. For example, in some aspects, the sample collection apparatus can be prepared such that it is substantially or completely free of nucleases (e.g., any enzymes that may degrade or destroy nucleic acids, such as RNA). As such, the sample collection apparatus may function to preserve the state of some or all of the nucleic acids contained within the biofluid, including intracellular and extracellular nucleic acids, such as RNA contained within exosomes.

In some embodiments, the sample collection apparatus may be a solid substance. In some aspects, the sample collection apparatus may be cellulose paper. Whatman paper, bibulous paper, cotton-based paper, cotton-based fabric, or any other substance that can be configured to receive the sample. By way of example only, in some aspects, the sample collection apparatus may be an RNA extraction strip card from FORTIUSBIO®. In other aspects, the sample collection apparatus may be a plasma-concentration device from Shimadzu®.

The term "nucleic acid" or "polynucleotide" as referred to herein comprises all forms of RNA (mRNA, miRNA, rRNA, tRNA, piRNA, ncRNA), DNA (genomic DNA or mtDNA), as well as recombinant RNA and DNA molecules or analogues of DNA or RNA generated using nucleotide analogues. The nucleic acids may be single stranded or double stranded. The nucleic acids may include the coding or non-coding strands. The term also comprises fragments of nucleic acids, such as naturally occurring RNA or DNA which may be recovered using one or more extraction methods disclosed herein. "Fragment" refers to a portion of a nucleic acid (e.g., RNA or DNA).

In some aspects, mRNA and/or miRNAs can be used in embodiments of the methodology. miRNAs are a large class of single strand RNA molecules of approximately 16-25 nucleotides, involved in post transcriptional gene silencing. Eighty percent of conserved miRNA show tissue-specific expression and play an important role in cell fate determination, proliferation, and cell death (Lee and Dutta. *Annu. Rev. Pathol. Mech. Dis.* 2009; 4: 199-227; Ross, Carlson and Brock, *Am J Clin Path* 2007: 128; 830-836). miRNAs arise from intergenic or intragenic (both exonic and intronic) genomic regions that are transcribed as long primary transcripts (pri-microRNA) and undergo a number of processing steps to produce the final short mature molecule (Massimo et al., *Current Op. in Cell Biol.* 2009: 21; 1-10).

The mature miRNAs suppress gene expression based on their complementarity to a part of one or more mRNAs usually in the 3' UTR site. The annealing of miRNA to the target transcript either blocks protein translation or destabilizes the transcript and triggers the degradation or both. Most of the miRNA action on target mRNA translation is based on the partial complementarity, therefore conceivably one miRNA may target more than one mRNA and many miRNAs may act on one mRNA (Ying at el., *Mol. Biotechnol.* 2008: 38; 257-268). In humans, approximately one-third of miRNAs are organized into clusters. A given cluster is likely to be a single transcriptional unit, suggesting a coordinated regulation of miRNAs in the cluster (Lee and Dutta. ibid).

The term "extracellular miRNA" means that the miRNA is found, located or circulates in a biofluid (biological fluid). For clarity, the term "extracellular miRNA" includes any one or more of miRNA found in exosomes or in other vesicles of cellular origin, miRNA originating from cells or more generally being of cellular origin, or being cellular isolates.

Biofluid can be, for example, blood, plasma, serum, urine, sputum, cerebrospinal fluid, milk, or ductal fluid, and can be fresh, frozen or fixed. For clarity, biofluid can comprise cells, cellular isolates, lysed cells or any type of cellular material. In some embodiments, the biofluid is blood, plasma or serum.

Although, there is currently no definitive source identified for extracellular miRNAs—i.e. a definitive source leading to miRNAs locating within biofluids—blood cells in particular reticulocytes, myeloid cells, lymphoid cells, platelets, cells from the liver, lungs and kidneys or lysed cells may release miRNAs into the circulation. Similarly, miRNAs may be discharged into biofluid/plasma following tissue damage, for example, following acute myocardial infarction.

There are a number of considerations when choosing protocols both upstream and downstream of NGS experiments. On the front end, purification methods, additives, and residuum can often inhibit the sensitive chemistries by which sequencing-by-synthesis is performed. On the back end, data handling, analysis software packages, and pipelines can also impact sequencing outcomes. The present invention provides methods of preparing biological samples (e.g., acellular biofluid samples) for small RNA sequencing.

The term "extraction" as used herein refers to any method for separating or isolating the nucleic acids from a sample, more particularly from a biological sample, such as blood. Nucleic acids such as RNA or DNA may be released, for example, by cell lysis. Moreover, in some aspects, extraction may also encompass the separation or isolation of extracellular RNAs (e.g., extracellular miRNAs) from one or more extracellular structures, such as exosomes.

Some embodiments of the invention include the extraction of one or more forms of nucleic acids from one or more samples. In some aspects, the extraction of the nucleic acids can provided using one or more techniques known in the art. For example, in some aspects, the extraction steps can be accomplished using the QIAAMP® RNA Blood Kit from QIAGEN® (e.g., for the isolation of total RNA) or EXORNEASY® Serum/Plasma Kit from QIAGEN® (e.g., for the isolation of intracellular and/or extracellular RNA). In other embodiments, methodologies of the invention can use any other conventional methodology and/or product intended for the isolation of intracellular and/or extracellular nucleic acids (e.g., RNA).

In one embodiment, the present invention provides methods of sequencing the full profile of nucleic acids (e.g., RNA) from a biological sample (e.g., blood). In certain aspects, the present invention provides a method of obtaining enough RNA from biofluid samples to perform RNA sequencing. With the prior art methods it was difficult to make sufficient scientifically verifiable conclusions from the biofluid samples because these conventional methodologies did not employ some of the advances contained herein, including perform RNA sequencing. As described herein, the inventors provide methods diagnosing and identifying diseases, conditions, and medical states as the expression of the nucleic acids change with various conditions.

The present invention also provides for the sequencing of RNA from samples (i.e., blood/plasma) from subjects. The RNA is useful as marker(s) for various diseases, conditions, and medical states as the expression of the RNAs change with disease severity/stage/outcome, age, etc. Commercial value resides in the ability to use a relatively small volume of sample from the subject (e.g., a drop of blood) to obtain significant clinical information. Moreover, additional value resides in the fact that multiple samples can be obtained from one or more subjects over a multitude of time intervals (e.g., samples obtained every minute, hour, day, week, month, etc.) such that those reviewing the results of the sequencing can gain a clearer resolution of the subject's medical state.

In some embodiments, the purified RNA from the biological sample is analyzed by Sequencing by Synthesis (SBS) techniques. SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in some of the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides. In methods using nucleotide monomers lacking terminators, the number of different nucleotides added in each cycle can be dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.). In preferred methods a terminator moiety can be reversibly terminating.

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.). However, it is also possible to use the same label for the two or more different nucleotides present in a sequencing reagent or to use detection optics that do not necessarily distinguish the different labels. Thus, in a doublet sequencing reagent having a mixture of A/C both the A and C can be labeled with the same fluorophore. Furthermore, when doublet delivery methods are used all of the different nucleotide monomers can have the same label or different labels can be used, for example, to distinguish one mixture of different nucleotide monomers from a second mixture of nucleotide monomers. For example, using the [First delivery nucleotide monomers]+[Second delivery nucleotide monomers] nomenclature set forth above and taking an example of A/C+(1/T), the A and C monomers can have the same first label and the G and T monomers can have the same second label, wherein the first label is different from the second label. Alternatively, the first label can be the same as the second label and incorporation events of the first delivery can be distinguished from incorporation events of the second delivery based on the temporal separation of cycles in an SBS protocol. Accordingly, a low resolution sequence representation obtained from such mixtures will be degenerate for two pairs of nucleotides (T/G, which is complementary to A and C, respectively; and C/A which is complementary to G/T, respectively).

Some embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons.

In another example type of SBS, cycle sequencing is accomplished by stepwise addition of reversible terminator nucleotides containing, for example, a cleavable or photo-bleachable dye label as described, for example, in U.S. Pat. Nos. 7,427,67, 7,414,1163 and 7,057,026, the disclosures of which are incorporated herein by reference. This approach is being commercialized by Solexa (now Illumina Inc.), and is also described in WO 91/06678 and WO 07/123,744 (filed in the United States Patent and Trademark Office as U.S. Ser. No. 12/295,337), each of which is incorporated herein by reference in their entireties. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

In other embodiments, Ion Semiconductor Sequencing is utilized to analyze the purified RNA from the sample. Ion Semiconductor Sequencing is a method of DNA sequencing based on the detection of hydrogen ions that are released during DNA amplification. This is a method of "sequencing by synthesis," during which a complementary strand is built based on the sequence of a template strand.

For example, a microwell containing a template DNA strand to be sequenced can be flooded with a single species of deoxyribonucleotide (dNTP). If the introduced dNTP is complementary to the leading template nucleotide it is incorporated into the growing complementary strand. This causes the release of a hydrogen ion that triggers a hypersensitive ion sensor, which indicates that a reaction has occurred. If homopolymer repeats are present in the template sequence multiple dNTP molecules will be incorporated in a single cycle. This leads to a corresponding number of released hydrogens and a proportionally higher electronic signal.

This technology differs from other sequencing technologies in that no modified nucleotides or optics are used. Ion semiconductor sequencing may also be referred to as ion torrent sequencing, proton-mediated sequencing, silicon sequencing, or semiconductor sequencing. Ion semiconductor sequencing was developed by Ion Torrent Systems Inc. and may be performed using a bench top machine. Rusk, N. (2011). "Torrents of Sequence," Nat Meth 8(1): 44-44. Although it is not necessary to understand the mechanism of an invention, it is believed that hydrogen ion release occurs during nucleic acid amplification because of the formation of a covalent bond and the release of pyrophosphate and a charged hydrogen ion. Ion semiconductor sequencing exploits these facts by determining if a hydrogen ion is released upon providing a single species of dNTP to the reaction.

For example, microwells on a semiconductor chip that each contain one single-stranded template DNA molecule to be sequenced and one DNA polymerase can be sequentially flooded with unmodified A, C, G or T dNTP. Pennisi, E. (2010). "Semiconductors inspire new sequencing technologies" Science 327(5970): 1190; and Perkel, J., "Making contact with sequencing's fourth generation" Biotechniques (2011). The hydrogen ion that is released in the reaction changes the pH of the solution, which is detected by a hypersensitive ion sensor. The unattached dNTP molecules are washed out before the next cycle when a different dNTP species is introduced.

Beneath the layer of microwells is an ion sensitive layer, below which is a hypersensitive ISFET ion sensor. All layers are contained within a CMOS semiconductor chip, similar to that used in the electronics industry. Each released hydrogen ion triggers the ISFET ion sensor. The series of electrical pulses transmitted from the chip to a computer is translated into a DNA sequence, with no intermediate signal conversion required. Each chip contains an array of microwells with corresponding ISFET detectors. Because nucleotide incorporation events are measured directly by electronics, the use of labeled nucleotides and optical measurements are avoided.

An example of a Ion Semiconductor Sequencing technique suitable for use in the methods of the provided disclosure is Ion Torrent sequencing (U.S. Patent Application Numbers 2009/0026082, 2009/0127589, 2010/0035252, 2010/0137143, 2010/0188073, 2010/0197507, 2010/0282617, 2010/0300559), 2010/0300895, 2010/0301398, and 2010/0304982), the content of each of which is incorporated by reference herein in its entirety. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and are attached at a resolution such that the fragments are individually resolvable. Addition of one or more nucleotides releases a proton (H+), which signal detected and recorded in a sequencing instrument. The signal strength is proportional to the number of nucleotides incorporated. User guides describe in detail the Ion Torrent protocol(s) that are suitable for use in methods of the invention, such as Life Technologies' literature entitled "Ion Sequencing Kit for User Guide v. 2.0" for use with their sequencing platform the Personal Genome Machine™ (PCG).

In some embodiments, as a part of the sample preparation process, "barcodes" may be associated with each sample. In this process, short oligonucleotides are added to primers, where each different sample uses a different oligo in addition to a primer.

The term "library", as used herein refers to a library of genome/transcriptome-derived sequences. The library may also have sequences allowing amplification of the "library" by the polymerase chain reaction or other in vitro amplification methods well known to those skilled in the art. The library may also have sequences that are compatible with next-generation high throughput sequencers such as an ion semiconductor sequencing platform.

The term "non-invasive" as used herein refers to a method of obtaining a sample from a subject in which the subject experiences little discomfort in the sample extraction process and the process itself may require little to know anesthesia or analgesia. For example, a non-invasive methodology may be a finger-prick procedure in which a small lancet is used to pierce the finger skin of a subject to obtain a drop of blood. Similar non-invasive methodologies can be used to obtain the sample.

In certain embodiments, the primers and barcodes are ligated to each sample as part of the library generation process. Thus during the amplification process associated with generating the ion amplicon library, the primer and the short oligo are also amplified. As the association of the barcode is done as part of the library preparation process, it is possible to use more than one library, and thus more than one sample. Synthetic nucleic acid barcodes may be included as part of the primer, where a different synthetic nucleic acid barcode may be used for each library. In some embodiments, different libraries may be mixed as they are introduced to a flow cell, and the identity of each sample may be determined as part of the sequencing process. Sample separation methods can be used in conjunction with sample identifiers. For example a chip could have 4 separate channels and use 4 different barcodes to allow the simultaneous running of 16 different samples.

As described in greater detail in the Examples section below, in some embodiments, after the RNA from the sample is sequenced, some embodiments provide methods of analyzing the data. For example, the analyzing steps of the methodology include steps such as processing the raw sequencing data/reads to remove information related to barcodes and adapters using technologies provided by Cutadapt and AlienTrimmer. Thereafter, the sequences can be aligned to a reference sequence using technologies such as STAR or Tophat and, after alignment, the data can be quantitated to generate numerical estimates of each gene's expression or "counts" provided by technologies like FeatureCounts or htseq-count. The principle issue in these matters is recognizing variance in these counts due to technical methods that may not represent biological significance.

In some conventional methodologies that may not employ biological samples of drop-sized volumes, the variance issue described above can be addressed with a generally simple expression cut off (i.e., any gene expression detected with >n counts usually exhibits low variance among replicates). This conventional methodology may not be suitable for small volume blood-based samples because the process of drying the small volume of blood in or on the sample collection apparatus may impart a non-uniform effect across RNA transcripts of variable length, possibly due to the RNA's biochemical structure and stability. In other words, the sample collection, drying, and storing process can create data that is difficult to analyze and/or rely upon when making clinical determinations.

In order to address the aforementioned issue, the inventors have started to survey the stability of different RNAs in collected samples (e.g., dried blood spots) by sequencing technical replicates and calculating the coefficient of variance (CV) for each transcript. By calculating the CV, the inventors were able to gather information related to each RNA's stability during the drying process and determine each RNA's potential accuracy as a biomarker. The CV value for each RNA is then employed in a two-step filtering process.

The first step of this analytical process includes the creation of a database of the CV values for one or more of the RNAs obtained from the samples. The database includes the CV values using non-dried blood spot RNA sequencing data to interrogate a dozen technical replicates of a control RNA sample. In some aspects, the control RNA sample can be from a known cell type, such as the HEX cell line. This interrogation process allows the investigators to filter subject (e.g., human) RNA transcripts exhibiting high variance likely due only to technical reasons because the replicates are technical in nature, rather than biological.

The second step of this filtering approach includes creating relatively specific CV databases for each sample type and methods of extraction, library preparation, sequencing methodology, etc. The information in these specific CV databases can be used to filter sample-/project-specific technical variance so that the best RNAs can be selected as markers for medical purposes. Moreover, some aspects of this two-step analytical methodology can be employed with other RNA sequencing-based methodologies.

Embodiments of the invention provide a method of analyzing a sample from a subject. Some aspects include obtaining a sample contained on and/or within a sample collection apparatus. Thereafter, nucleic acids can be obtained from the sample and the nucleic acids (e.g., intracellular and/or extracellular RNA) can be processed and sequenced to obtain information about the biological state of the subject. The data obtained from the sequencing steps can be processed using a two-step algorithm to determine which nucleic acids can provide the most reliable information.

Relative to conventional technologies, some embodiments of the invention offer improvements. For example, some embodiments require as a little as a single drop of blood contained/dried on a sample collection apparatus to gain valuable insight into the biological/medical state of the subject. As such, the requirement for obtaining one or more vials of blood can be removed as a barrier to obtaining accurate information about a subject. Moreover, subjects/patients can largely obtain these samples themselves. Although a medical professional does have the capability of obtaining these small volume samples, subjects without medical training can be instructed on how to obtain the samples. For example, one or more drops of blood can be obtained from a subject using known methodologies, such as a finger stick that is now currently used to regularly obtain blood for blood-glucose testing. As such, embodiments of this invention provide simplistic sample collection opportunities for subjects. Further, subjects can obtain regular longitudinal samples because of the relatively non-invasive nature of some embodiments of the invention and the ease with which subjects can obtain the sample(s). In other words, subjects can provide multiple samples obtained over varying time periods to medical professionals. For example, a subject can take a single drop of blood each hour of a day (i.e., 24 samples) and allow that blood to dry on the sample collection apparatus and provide that apparatus for nucleic-acid extraction and processing for biological/medical state analysis. This can provide a medical professional with much greater resolution in terms of assessing the biological/medical state of the subject.

Some embodiments of the inventive methodology can be used with any specific applications that may require only a limited volume of sample. Some embodiments of the invention can be used m conjunction with testing subjects that may not be able to provide a sample of significant volume. For example, some embodiments may be used in conjunction with the testing of neonates and other embodiments may be used in conjunction with the testing of one or more types of endurance athletes. In particular, embodiments of the invention can be used in testing neonates because of the limited source of sample (e.g., blood) and the relatively non-invasive nature of the method. Moreover, embodiments of the invention can be used in testing athletes, such as endurance athletes, because the relatively small volume of sample necessary for use in conjunction with the method will not significantly impact the blood volume of the athlete.

In addition, the relatively small volume of sample (e.g., blood) that is required by the method may further enable multiple samplings of the respective subjects.

Some embodiments of the invention may also be employed in other contexts. For example, the methodology can be used to potentially assess the sex of a child in utero. Specifically, it is known that extracellular DNA of a fetus can cross the placenta and enter the circulation of the mother. In the event that the fetus is male, embodiments of the methodology can be used to detect one or more RNA transcripts associated with the Y chromosome. Other embodiments of the invention can be used in conjunction with any other applications that can accommodate relatively small volumes of sample and/or require multiple sample acquisition events.

In one aspect, described herein is an assay comprising: measuring, in a sample obtained from a subject, the level of at least one miRNA selected from the group consisting of: miR-10b-5p; miR-151b; miR-291-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; miR-30a-3p; miR-132-5p, miR-212-3p, miR-212-5p, miR-145-5p; and miR-29a-5p and determining that the subject is at increased risk of Parkinson's Disease developing or progressing if the level of an miRNA selected from the group consisting of miR-151b; miR-5690; miR-516b-5p; miR208b-3p; miR106a-5p; and miR-363-3p; miR-30a-3p; and miR-29a-5p is increased relative to a reference, and determining that the subject is at decreased risk of Parkinson's Disease developing or progressing if the level of the miRNA is not increased relative to a reference; determining that the subject is at increased risk of Parkinson's Disease developing or progressing if the level of an miRNA selected from the group consisting of: miR-10b-5p; miR-29b-2-5p; miR-329-3p; miR-6511a-5p; miR-4526; miR-129-1-3p; miR-129-2-3p; and miR-132-3p; miR-132-5p; miR127-3p; miR212-3p; miR-1224-5p; miR16-2-3p; miR-1294 miR-132-5p, miR-212-3p, miR-212-5p, and miR-145-5p; is decreased relative to a reference, and determining that the subject is at decreased risk of Parkinson's Disease developing or progressing if the level of the miRNA is not decreased relative to a reference; wherein increased risk of Parkinson's Disease developing or progressing comprises developing Parkinson's Disease at a younger age; death due to Parkinson's Disease at a younger age; development of dementia; development of dementia at an earlier age; or onset of motor symptoms at an earlier age when compared to other individuals with Parkinson's Disease who do not have such a level of the miRNA.

In one aspect, described herein is a method comprising: measuring, in a sample obtained from a subject, the level of at least one miRNA selected from the group consisting of: miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; milt-1224-5p; miR16-2-3p; miR-1294; miR-30a-3p; miR-132-5p, milt-212-3p, miR-212-5p, miR-145-5p; and miR-29a-5p and determining that the subject is at increased risk of Parkinson's Disease developing or progressing if the level of an miRNA selected from the group consisting of: miR-15 b; miR-5690; miR-516b-5p; miR208b-3p; miR106a-5p; and miR-363-3p; miR-30a-3p; and miR-29a-5p is increased relative to a reference, and determining that the subject is at decreased risk of Parkinson's Disease developing or progressing if the level of the miRNA is not increased relative to a reference; determining that the subject is at increased risk of Parkinson's Disease developing or progressing if the level of an miRNA selected from the group consisting of: miR-10b-5p; miR-29b-2-5p; miR-329-3p; miR-6511a-5p; miR-4526; miR-129-1-3p; miR-129-2-3p; and miR-132-3p; miR-132-5p; miR127-3p; miR212-3p; milt-1224-5p; miR16-2-3p; miR-1294; miR-132-5p, miR-212-3p, miR-212-5p, and miR-145-5p is decreased relative to a reference, and determining that the subject is at decreased risk of Parkinson's Disease developing or progressing if the level of the miRNA is not decreased relative to a reference; and administering a treatment for Parkinson's Disease if the subject is at increased risk of Parkinson's Disease developing or progressing; wherein increased risk of Parkinson's Disease developing or progressing comprises developing Parkinson's Disease at a younger age; death due to Parkinson's Disease at a younger age; development of dementia; development of dementia at an earlier age; or onset of motor symptoms at an earlier age when compared to other individuals with Parkinson's Disease who do not have such a level of the miRNA.

In some embodiments, a treatment for Parkinson's Disease can be selected from the group consisting of: Levodopa agonists; dopamine agonists; COMT inhibitors; deep brain stimulation; MAO-B inhibitors; lesional surgery; regular physical exercise; regular mental exercise; improvements to the diet; and Lee Silverman voice treatment. In some embodiments, a treatment for Parkinson's Disease can comprise administering an agent that modulates (e.g., increases or decreases) the abnormal level or expression of at least one of the said miRNAs.

In one aspect, described herein is an assay comprising: measuring, in a sample obtained from a subject, the level of at least one miRNA selected from the group consisting of: miR-10b-5p; miR196a-5p; miR196b-5p; miR615-3p; and miR1247-5p; miR106a-5p; miR363-3p; miR-129-1-3p and miR-132-3p; and determining that the subject is at increased likelihood of Huntington's Disease developing at an earlier age or progressing more rapidly if the level of an miRNA selected from the group consisting of: miR-10b-5p; miR196a-5p; miR196b-5p; miR615-3p; miR1247-5p; miR106a-5p; and miR363-3p is increased relative to a reference, and determining that the subject is at decreased likelihood of Huntington's Disease developing at an earlier age or progressing more rapidly if the level of the miRNA is not increased relative to a reference; or determining that the subject is at increased likelihood of Huntington's Disease developing at an earlier age or progressing more rapidly if the level of an miRNA selected from the group consisting of: miR-129-1-3p and miR-132-3p; is decreased relative to a reference, and determining that the subject is at decreased likelihood of Huntington's Disease developing at an earlier age or progressing more rapidly if the level of the miRNA is not decreased relative to a reference; wherein increased likelihood of Huntington's Disease developing at an earlier age or progressing more rapidly comprises developing Huntington's Disease at a younger age; death due to Huntington's Disease at a younger age, and/or becoming more severely disabled at a younger age as compared to other individuals with Huntington's Disease who do not have such a level of the miRNA.

In one aspect, described herein is a method comprising: measuring, in a sample obtained from a subject, the level of at least one miRNA selected from the group consisting of: miR-10b-5p; miR196a-5p; miR196b-5p; miR615-3p; miR1247-5p; miR106a-5p; miR363-3p; miR-129-1-3p and miR-132-3p; and determining that the subject is at increased likelihood of Huntington's Disease developing at an earlier age or progressing more rapidly if the level of an miRNA selected from the group consisting of: miR-10b-5p; miR196a-5p; miR196b-5p; miR615-3p; miR1247-5p; miR106a-5p; and miR363-3p is increased relative to a reference, and determining that the subject is at decreased likelihood of Huntington's Disease developing at an earlier age or progressing more rapidly if the level of the miRNA is not increased relative to a reference; or determining that the subject is at increased likelihood of Huntington's Disease developing at an earlier age or progressing more rapidly if the level of an miRNA selected from the group consisting of: miR-129-1-3p and miR-132-3p; is decreased relative to a reference, and determining that the subject is at decreased likelihood of Huntington's disease developing at an earlier age or progressing more rapidly if the level of the miRNA is not decreased relative to a reference; and administering a treatment for Huntington's Disease if the subject is at increased likelihood of Huntington's disease developing at an earlier age or progressing more rapidly wherein increased likelihood of Huntington's disease developing at an earlier age or progressing more rapidly comprises developing Huntington's Disease at a younger age; death due to Huntington's Disease at a younger age; and/or becoming more severely disabled at a younger age, when compared to other individuals with Huntington's Disease who do not have such a level of the miRNA.

In some embodiments, a treatment for Huntington's Disease can be selected from the group consisting of: regular physical exercise; regular mental exercise; improvements to the diet; or administering creatine monohydrate, coenzyme Q10, sodium phenylbutyrate. In some embodiments, a treatment for Huntington's Disease can comprise administering an agent that modulates (e.g. increases or decreases) the abnormal level or expression of at least one of the miRNAs whose abnormal levels and/or expression is described herein as indicating an increased risk or likelihood of Huntington's Disease developing or progressing.

Additional aspects of assaying specific miRNAs that indicate neurodegenerative disease are disclosed in U.S. patent application Ser. No. 14/595,783, which is hereby incorporated by reference.

The present invention offers several advantages over other methods and assays. Isolating RNA with the EXORNEASY® kit enriches for extracellular RNA biomarkers. These extracellular RNA biomarkers are rich in information and can be used for various applications such as determining fetal sex from a maternal dried blood sample. Moreover, using RNA sequencing instead of a microarray hybridization technology expands the flexibility and possible uses of the method: RNA sequencing does not require species- or transcript-specific probes; and it can detect novel transcripts, gene fusions, single nucleotide variants (SNVs), and indels. RNA sequencing is a digital technology and therefore has a broader dynamic range whereas microarrays are limited by background at the low end and signal saturation at the high end. The advantages of RNA sequencing over microarray analysis are further explained in Zhao, S. et al., (2014) Comparison of RNA-Seq and Microarray in Transcriptome Profiling of Activated T Cells, PUS ONE 9:e78644; and Hrdlickova, R., et at (2016) RNA-Seq Methods for Transcriptome Analysis, WIREs RNA doi:10.1002/wrna.1364.

The gene names listed herein, including the miRNA names, are common names. NCBI Gene ID numbers and/or sequences for each of the genes given herein can be obtained by searching the "Gene" Database of the NCBI (available on the World Wide Web at http://www.ncbi.nlm.nih.gov/) using the common name as the query and selecting the first returned *Homo sapiens* gene. Alternatively, sequences for each of the miRNAs given herein can be obtained by searching the miRbase (available on the world wide web at mirbase.org) using the common name as the query and selecting the first returned *Homo sapiens* miRNA.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Example 1. Dried Blood Spot Assay Development

Materials and Methods
Sample Collection

A first set of samples were collected as undried blood samples that were added directly to the first buffer listed below (i.e., wet blood drops/droplets). Another set of samples were obtained as a single drop of a subject's blood on a sample collection apparatus obtained from FORTIUSBIO®. Thereafter, the blood spot was allowed to dry on the FORTIUSBIO® sample collection apparatus. After drying, the dried blood spot was removed from the sample collection apparatus and processed as described below.

In addition, samples were obtained from a subject before, during, and after vigorous exercise (e.g., biking). In particular, a drop of blood was obtained from the subject at 5:30 AM and 9:30 AM (pre-exercise samples) and the subject started exercising at 10:00 AM. After initiation of exercise at 10:00 AM, samples were obtained at ten-minute intervals for during the one hour exercise session (a total of 6 samples). Then, post-exercise samples were obtained at noon, 1:00 PM, 2:00 PM, and 3:00 PM. All samples were obtained using a finger-puncture technique in which a single drop of blood from the subject's finger was applied to a sample collection apparatus (i.e., RNA collection paper from FORTIUSBIO®.

RNA Extraction

The investigators extracted RNA using two different commercially available kits—the QIAAMP® RNA Blood Kit from QIAGEN® (e.g., for the isolation of total RNA) and EXORNEASY® Serum/Plasma Kit from QIAGEN® (e.g., for the isolation of intracellular and/or extracellular RNA). The investigators modified the protocols as described below. In particular, the investigators did not perform the initial step of lysing all non-erythrocyte cells.

The protocol used for the EXORNEASY® kit is included below in its stage as modified by the investigators:

Remove a portion of the sample that has been dried on the sample collection apparatus and mix with 0.9% saline. Allow the sample to spin in the saline solution for approximately one hour.

After spinning/mixing for an hour, the sample collection apparatus is removed and the process proceeds as follows.

Add a 1:1 volume of buffer XBP and sample. Immediately invert tube 5 times to mix.

Place sample/XBP mix onto exoEasy spin column. Spin for 1 minute at 500 g. Discard flow-through.

Add 10 mL XWP and spin at 3,000-5,000 g for 5 minutes. Discard flow-through and collection tube.

Transfer spin column to a new collection tube.

Add 700 ul QIAzol to the membrane. Spin at 3,000-5,000 g for 5 minutes to collect the lysate and transfer to a 2 mL tube.

Vortex the lysate briefly and incubate at room temperature for 5 minutes.

Add 90 ul chloroform to the lysate. Cap tube and shake for 15 seconds.

Incubate at room temperature for 3 minutes.

Centrifuge 15 minutes at 12,000 g at 4° C.

Transfer upper aqueous phase to a new collection tube. Avoid transfer of any interphase material.

Add 2:1 volume of 100% ethanol to sample. Mix thoroughly by pipetting up and down several times.

Pipette 700 ul sample, including precipitate, if formed, into an RNeasy MinElute spin column in a 2 mL collection tube. Close lid and centrifuge at 9,000×g for 15 seconds at room temperature. Discard flow-through.

Repeat step 12 using the remainder of the sample. Discard flow-through.

Add 700 ul Buffer RWT to RNeasy MinElute spin column. Close lid and centrifuge at 9,000×g for 15 seconds. Discard flow-through.

Pipette 500 ul Buffer RPE onto RNeasy MinElute spin column. Close lid and centrifuge at 9,000×g for 15 seconds. Discard flow-through.

Pipette 500 ul Buffer RPE onto RNeasy MinElute spin column. Close lid and centrifuge at 9,000×g for 2 minutes. Discard the flow-through and collection tube.

Place spin column into new 2 mL collection tube. Open lid of spin column and centrifuge at full speed (16,000×g) for 5 minutes to dry the membrane. Discard the collection tube with flow-through.

Place RNeasy MinElute spin column in a new 1.5 mL collection tube. Add 15 ul RNase-free water directly to center of membrane. Close lid and let column stand for 1 minute. Centrifuge for 1 minute at full speed (16,000×g) to elute RNA. Repeat once more for a total volume of 30 ul. This final step has been optimized compared to the manufacturer's recommended elution process. As such, this step provides the investigators with improved elution.

The protocol used for the QIAAMP® kit is included below in its stage as modified by the investigators, with an optional DNAse treatment included as well:

Add 10 ul B-Mercaptoethanol (BME) per 1 mL Buffer RLT before beginning

Add Buffer RLT to the sample (i.e., dried blood spot or DBS) (350 ul). Vortex or pipet to mix and allow to rotate at room temperature for one hour.

After spinning/mixing for an hour, the sample collection apparatus is removed and the process proceeds as follows.

Pipet lysate directly into a QIAshredder spin column in a 2 mL collection tube and centrifuge for 2 minutes at maximum speed (16,000×g) to homogenize. Discard the QIAshredder spin column and save the homogenized lysate.

Add 1 volume (350 ul) of 70% ethanol to the homogenized lysate and mix by pipetting. Do not centrifuge.

Pipet sample, including any participate which may have been formed, into a new QIAAMP® spin column in a 2 mL collection tube. Centrifuge for 15 seconds at 9,000×g. Maximum loading volume is 700 ul. If the volume of the sample exceeds 700 ul, successively load aliquots onto the QIAAMP® spin column and centrifuge as above. Discard flow-through. (Optional on-column DNase digestion after this step. See below.)

Transfer the QIAAMP® spin column into a new 2 mL collection tube. Pipette 700 ul of Buffer RW1 into the spin column and centrifuge for 15 seconds at 9,000×g to wash. Discard flow-through.

Place QIAAMP® spin column in a new 2 mL collection tube. Pipette 500 ul of Buffer RPE into the spin column and centrifuge for 15 seconds at 9,000×g. Discard flow-through.

Carefully open QIAAMP® spin column and add 500 ul of Buffer RPE. Close cap and centrifuge at full speed (16,000×g) for 3 minutes.

Place QIAAMP® spin column in a new 2 mL collection tube and discard the old collection tube with the filtrate. Centrifuge at full speed (16,000×g) for 1 minute.

Transfer QIAAMP® spin column into a 1.5 mL microcentrifuge tube and pipet 15 ul of RNase-free water directly onto the QIAAMP® membrane. Incubate for 1 minute before centrifuging for 1 minute at 9,000×g to elute the RNA. Repeat once more for a total volume of 30 ul. This final step has been optimized compared to the manufacturer's recommended elution process. As such, this step provides the investigators with improved elution.

On-Column DNase

Add 350 ul Buffer RW1 to the QIAAMP® spin column. Close lid and centrifuge for 15 seconds at 9,000×g to wash the membrane. Discard the flow-through.

Add 10 ul DNase I Stock solution to 70 ul Buffer RDD. Mix by inverting the tube and centrifuge briefly to collect residual liquid from the top and sides of the tube.

Add the DNase I incubation mix (80 ul) directly to the QIAAMP® spin column membrane and place at room temperature for 15 minutes.

Add 350 ul Buffer RW1 to the QIAAMP® spin column. Close the lid and centrifuge for 15 seconds at 9,000×g. Discard flow-through. Continue with the first Buffer RPE wash step in the protocol.

The preceding protocols provide embodiments of the present invention. These protocols are capable of further modifications and these applications are intended to cover any variations, uses, or adaptations of the invention following, in general, the principles of the invention and including such departures from the present disclosure as come within known or customary practice within the art to which the invention pertains.

Determination of RNA Yield

Quantification of total RNA yield was determined by Quant-iT RiboGreen RNA reagent (Invitrogen) utilizing the low-range assay in a 200-µL total volume in the 96-well format (Costar). This protocol allows for quantification of 1-50 pg/µL, the linearity of which is maintained in the presence of common post-purification contaminants such as salts, ethanol, chloroform, detergents, proteins, and agarose (Jones L J, Yue S T, Cheung C Y, Singer V L. 1998. RNA quantitation by fluorescence-based solution assay: RiboGreen reagent characterization. Anal Biochem 265: 368-374.). Individual samples were assayed in triplicate, and the means were calculated. The three replicates from the same treatment were averaged. The investigators used the low-range assay (1-50 pg/µL) in a 200-µL total volume of working reagent in a 96-well format and read on a plate reader (BioteK Synergy HT).

In addition, sample quality was assessed using an Agilent bioanalyzer. In particular, RNA quality was determined by capillary electrophoresis of the extracted RNA through the use of an Agilent Bioanalyzer. As is customary, the RNA quality is quantified as a RIN, wherein the RIN is calculated by an algorithmic assessment of the amount of various RNAs presented within the extracted RNA. High-quality cellular RNA generally exhibits a RNA value approaching 10.

RNA Sequencing

A portion of the extracted nucleic acids was introduced into the TruSeq Small RNA Sample reagents, followed by 15 cycles of PCR to amplify the library. The investigators clustered a single read v3 flow cell and performed RNA deep sequencing on the HiSeq 2000 using the RNA isolated from the aliquots of sample.

Sequencing Data Analysis

CV values for respective RNAs were calculated. By calculating the CV, the inventors were able to gather information related to each RNAs stability during the drying process and determine each RNA's potential accuracy as a biomarker. The CV value for each RNA is then employed in a two-step filtering process.

The first step of this analytical process includes the creation of a database of the CV values for one or more of the RNAs obtained from the samples. The database includes the CV values using non-dried blood spot RNA sequencing data to interrogate a dozen technical replicates of a control RNA sample. In some aspects, the control RNA sample can be from a known cell type, such as the HEK cell line. This interrogation process allows the investigators to filter subject (e.g., human) RNA transcripts exhibiting high variance likely due only to technical reasons because the replicates are technical in nature, rather than biological.

The second step of this filtering approach includes creating relatively specific CV databases for each sample type and methods of extraction, library preparation, sequencing methodology, etc. The information in these specific CV databases can be used to filter sample-/project-specific technical variance so that the best RNAs can be selected as markers for medical purposes. Moreover, some aspects of this two-step analytical methodology can be employed with other RNA sequencing-based methodologies.

Results

Figure 2:
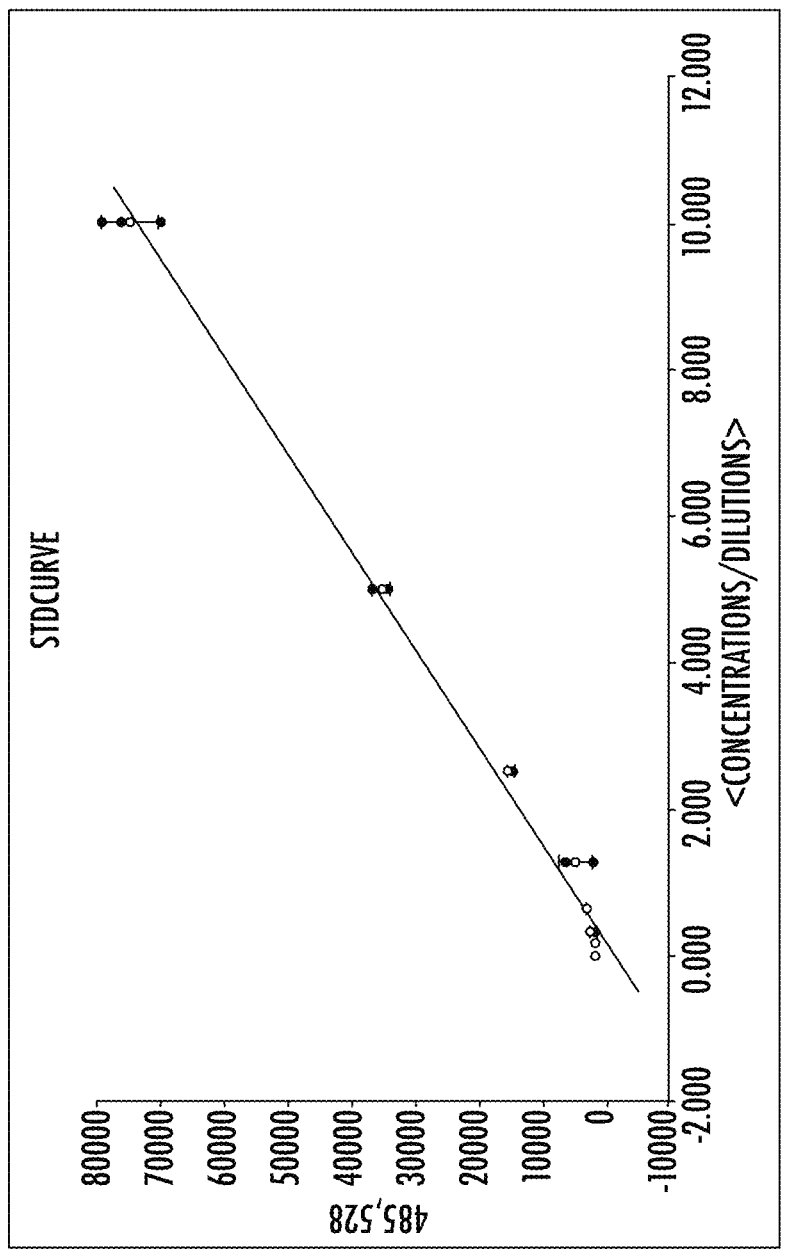
FIG. 2 depicts the standard curve used to calculate the RNA total yields in Table 2.

As an initial matter, after extraction from the samples, the quality of the RNA was assessed using an Agilent Bioanalyzer, as illustrated in FIGS. 5-14. First, in FIGS. 5 and 6 and Table 1, the investigators were able to demonstrate the relative quality and quantity of the RNA molecules isolated by the QIAAMP® and EXORNEASY® kits with the addition of only a drop of wet whole blood to the first step of the extraction process (i.e., rather than using a dried blood spot), as a control. The standard curve associated with Table 1 is shown in FIG. 1. The data shows that the investigators were able to isolate acceptable quality RNAs (FIGS. 5 and 6) and of a sufficient concentration (Table 1). Next, the inventors investigated the isolation of RNA using the QIAAMP® kit and dried blood spots that had been previously dried on a sample collection apparatus. The inventors performed the extractions with and without the DNA digestion step using DNase. The data shows that the investigators were able to isolate acceptable quality RNAs (FIGS. 7 and 8) and of a sufficient concentration (Table 2). The standard curve associated with Table 2 is shown in FIG. 2.

Figure 3:
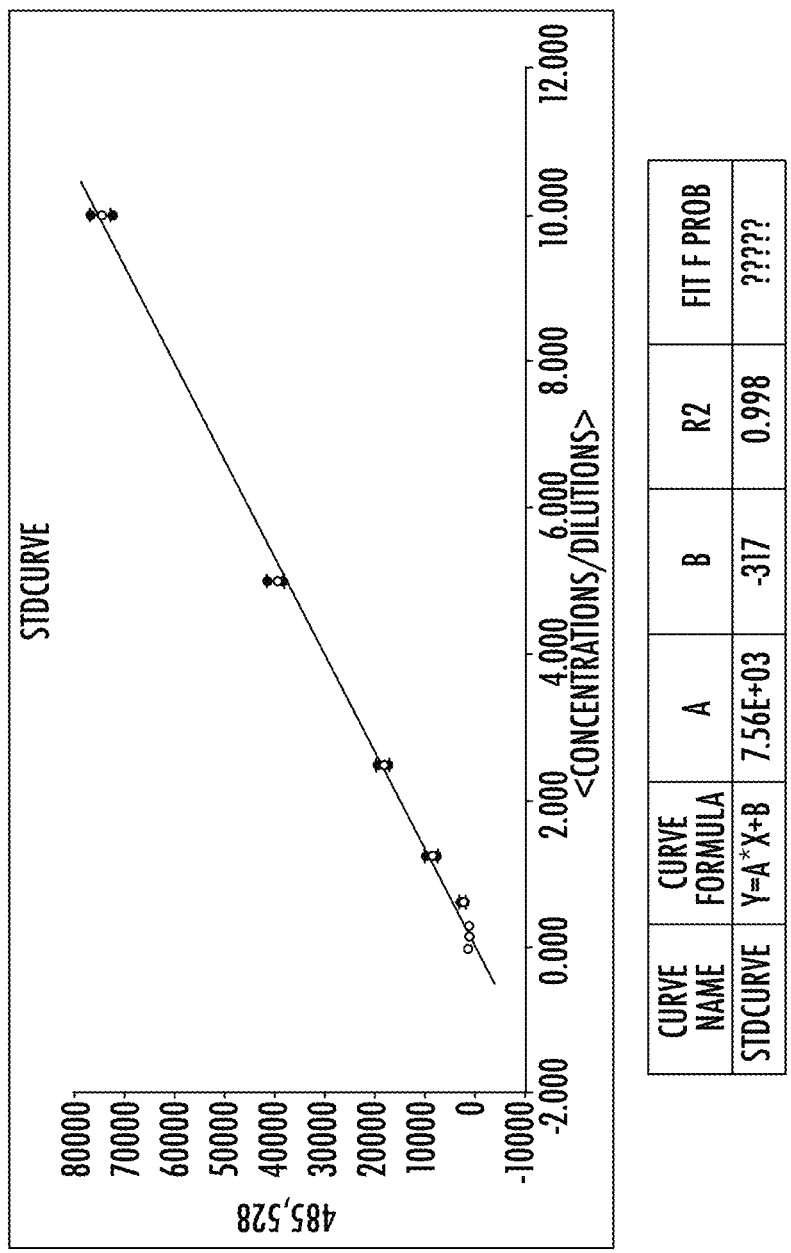
FIG. 3 depicts the standard curve used to calculate the RNA total yields in Table 3.
Figure 9:
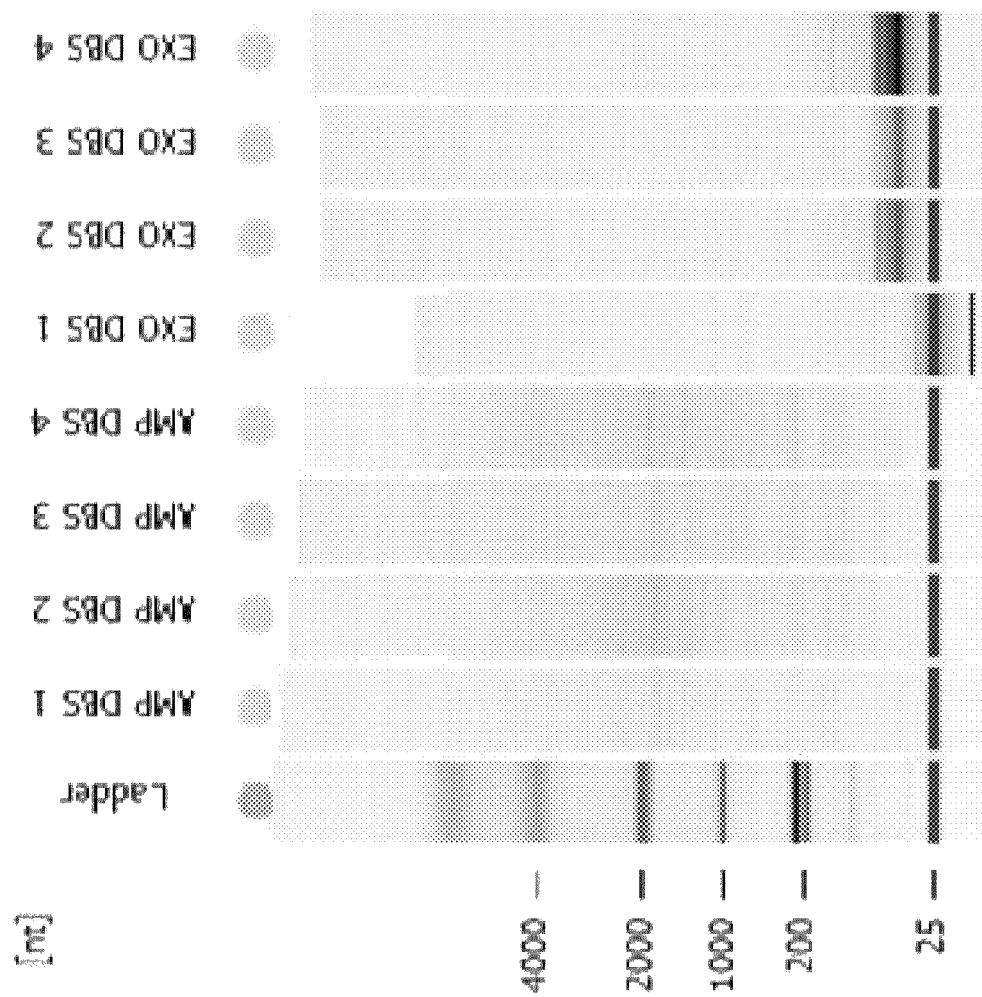
FIG. 9 depicts an assessment of the quality of RNA preparations from dried blood spots by capillary electrophoresis.
Figure 10:
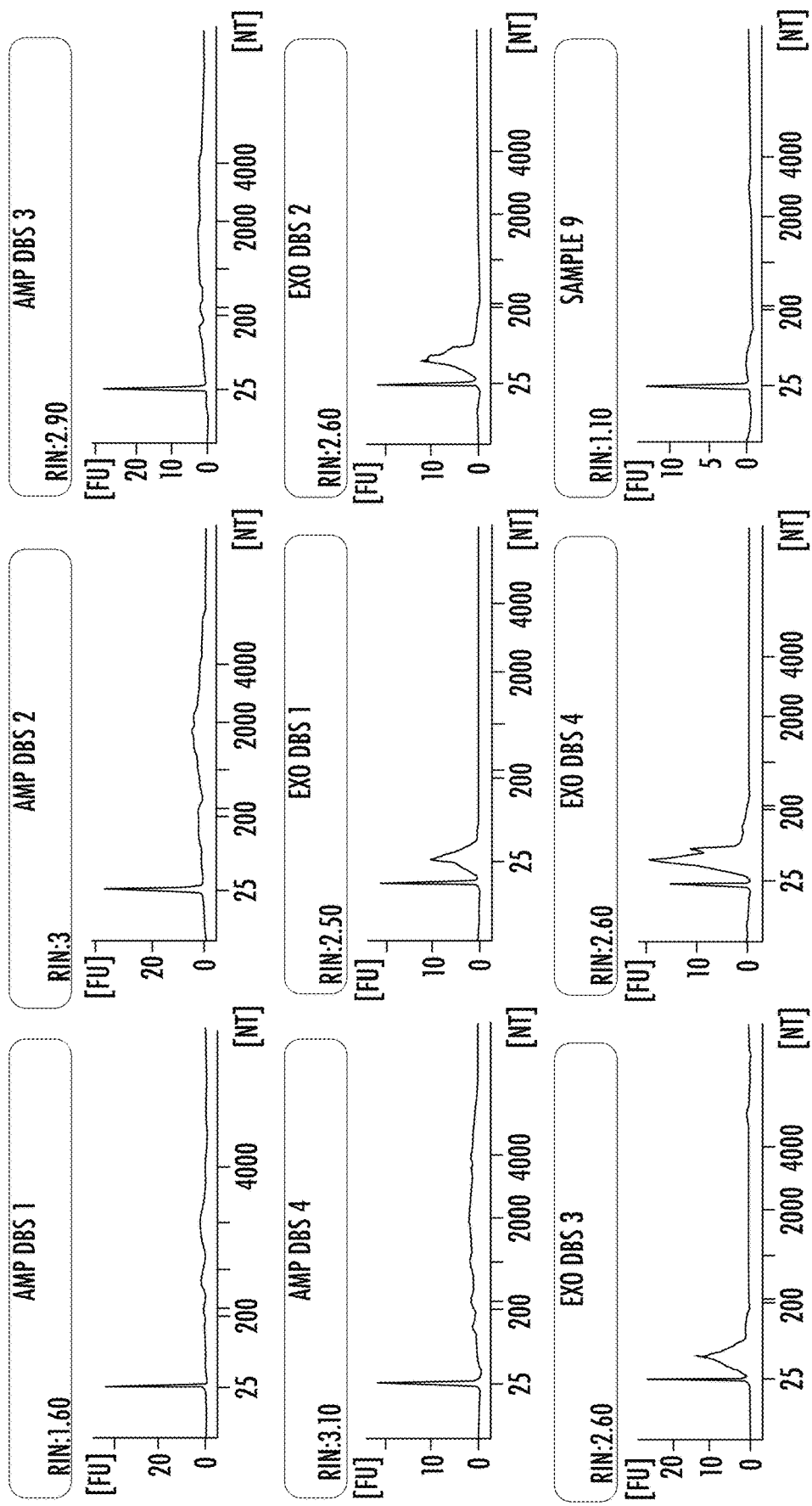
FIG. 10 depicts analysis of the integrity of RNA preparations from dried blood spots performed on an Agilent Bioanalyzer. The amount of RNA is depicted in FU for RNA molecules ranging in size from <25 nt to >4,000 nt.
Figure 11:
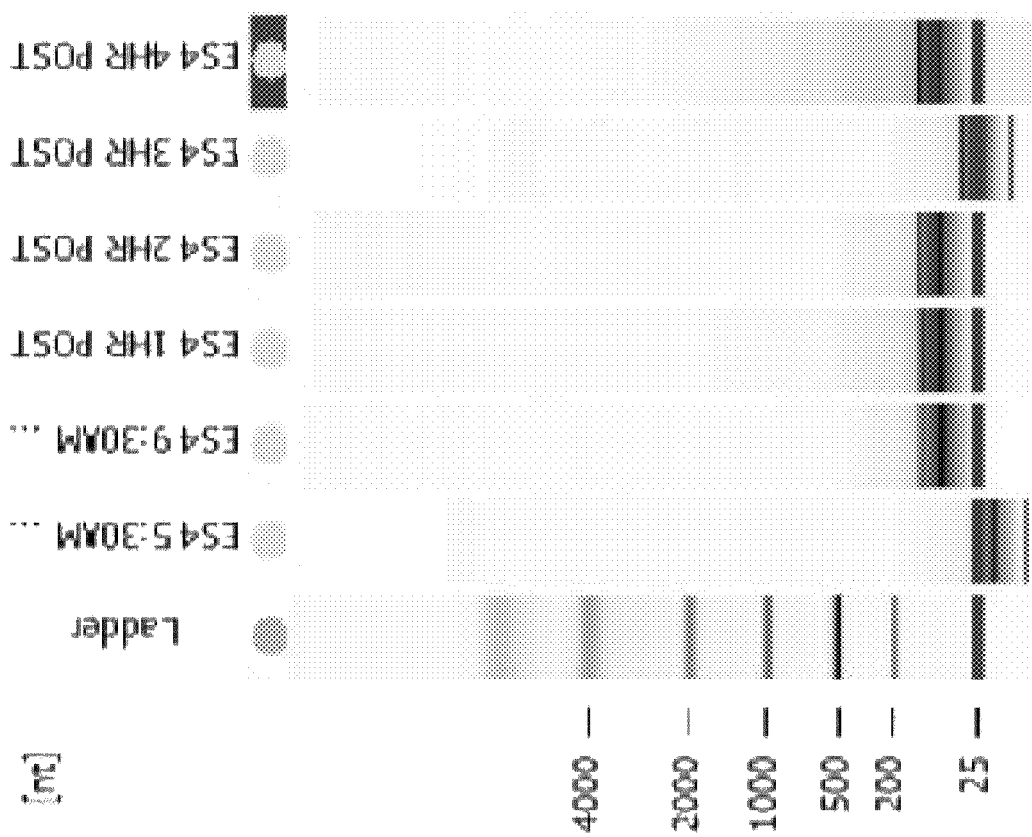
FIG. 11 depicts an assessment of the quality of RNA preparations from dried blood spots collected from a subject at several time points before and after exercising by capillary electrophoresis.
Figure 12:
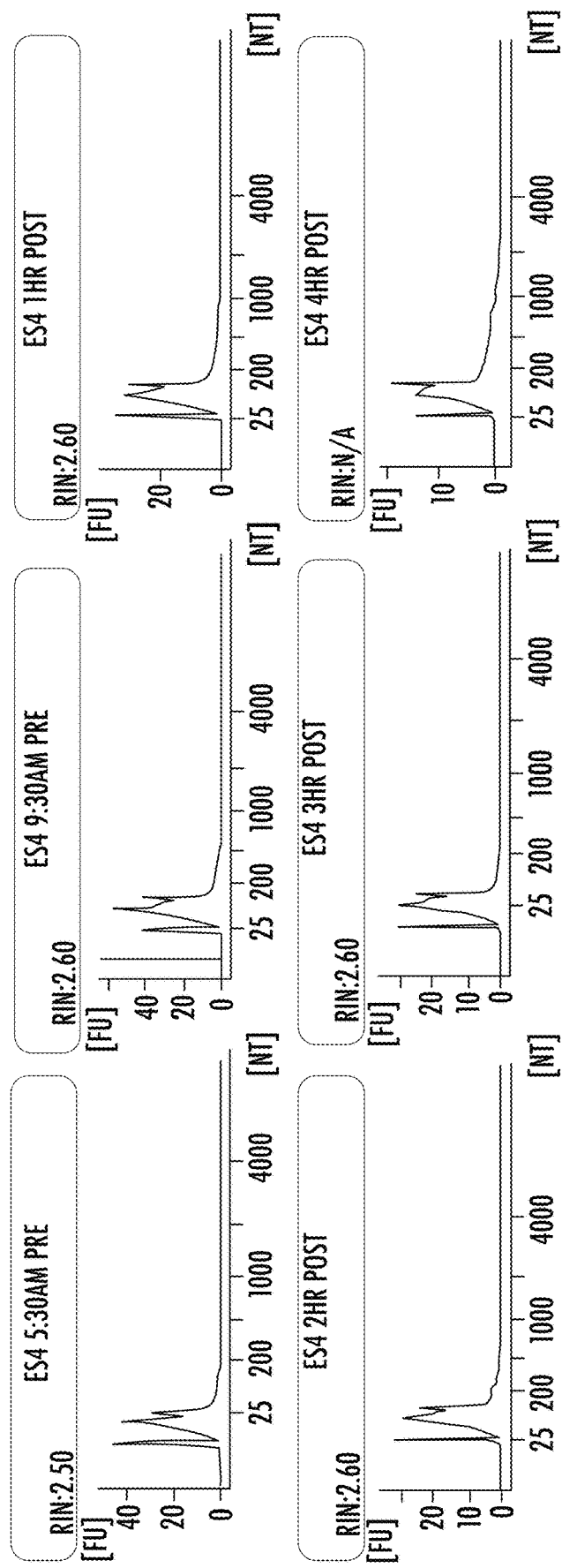
FIG. 12 depicts analysis of the integrity of RNA preparations from dried blood spots collected from a subject at several time points before and after exercising performed on an Agilent Bioanalyzer. The amount of RNA is depicted in FU for RNA molecules ranging in size from <25 nt to >4,000 nt.
Figure 13:
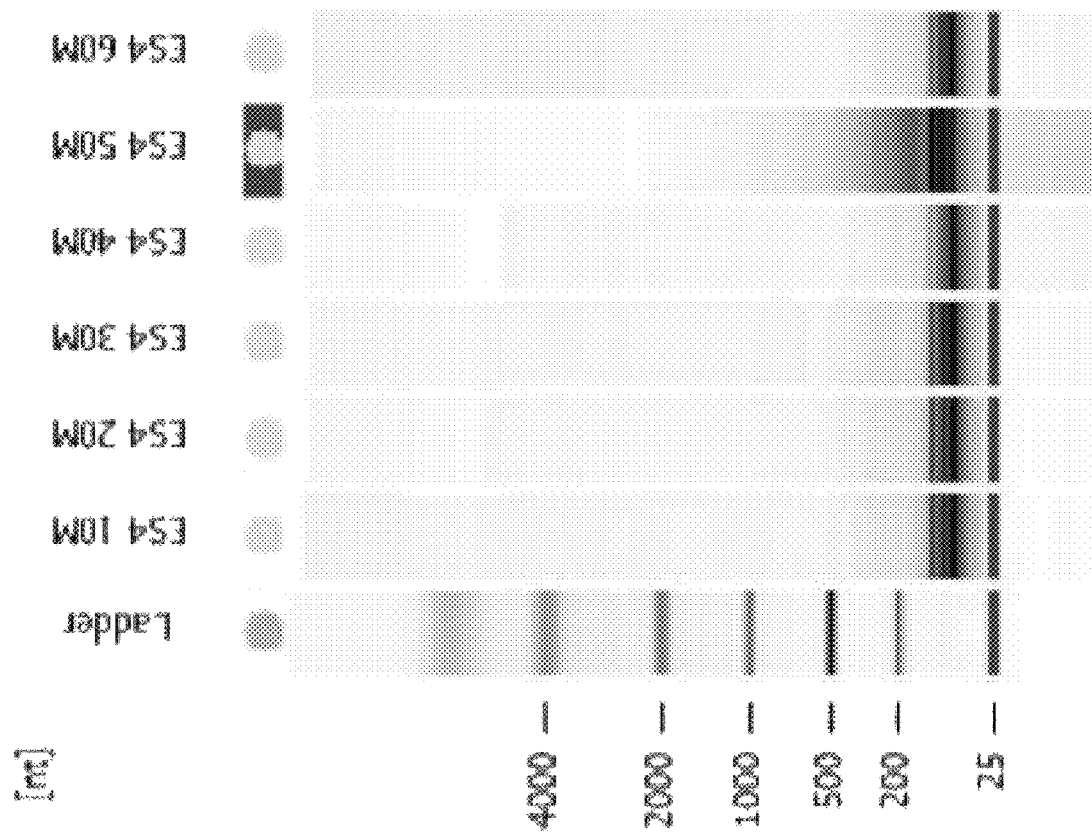
FIG. 13 depicts an assessment of the quality of RNA preparations from dried blood spots collected from a subject at several time points before and after exercising by capillary electrophoresis.
Figure 14:
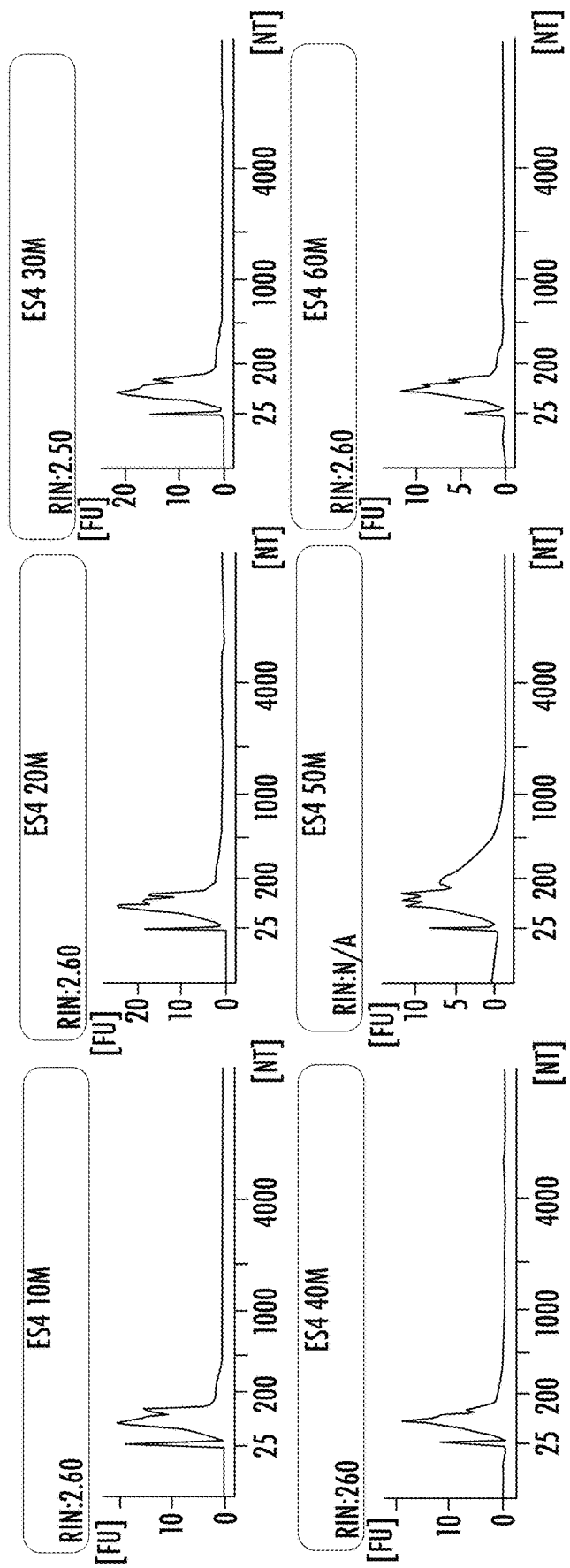
FIG. 14 depicts analysis of the integrity of RNA preparations from dried blood spots collected from a subject at several time points before and after exercising performed on an Agilent Bioanalyzer. The amount of RNA is depicted in FU for RNA molecules ranging in size from <25 nt to >4,000 nt.
Figure 15A:
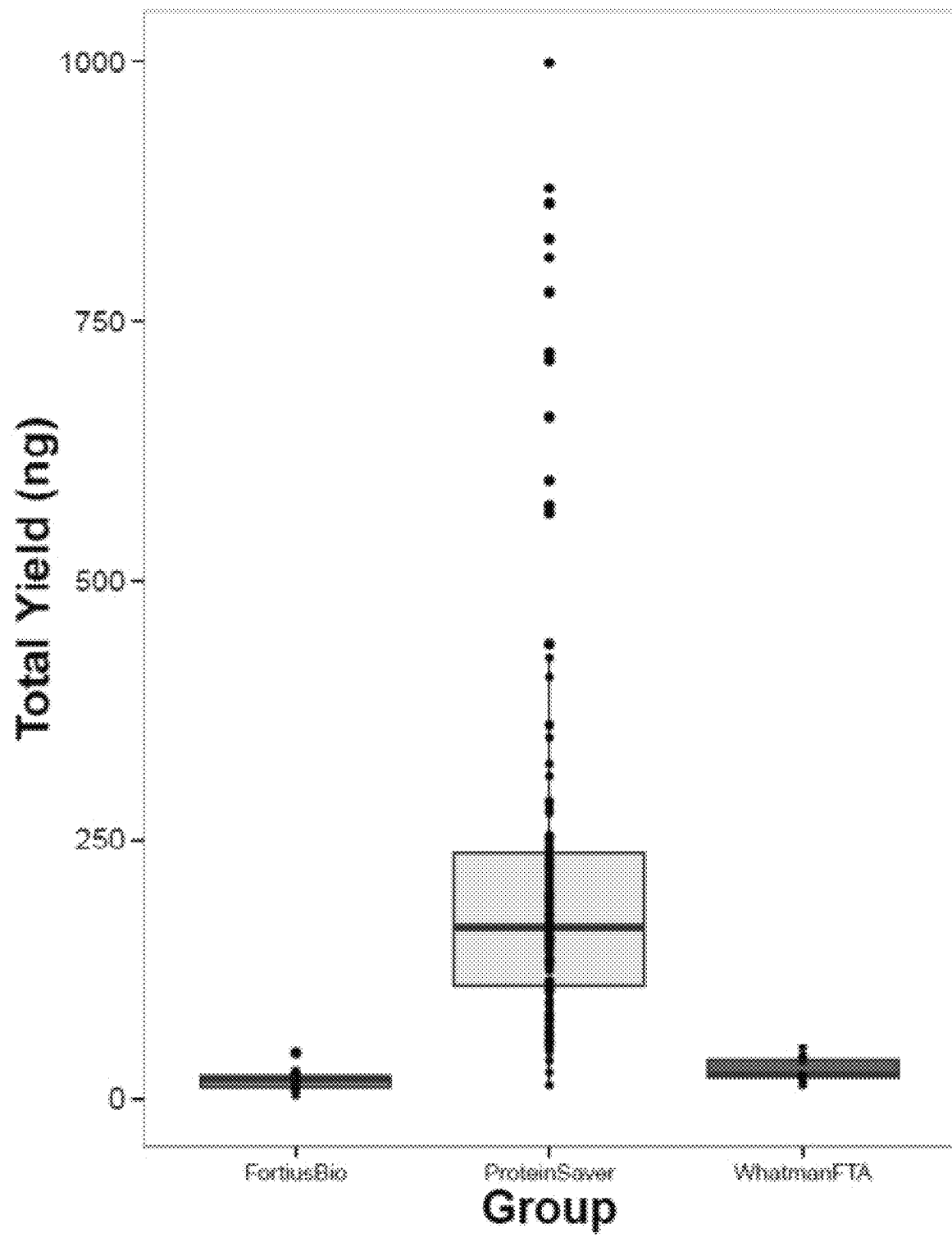
FIG. 15A depicts box plots of total RNA yield values from dried blood samples collected on FORTIUSBIO® RNA-SOUND™ blood sampling cards, WHATMAN® 903 Protein Saver cards or WHATMAN® FTA® non-indicating Elute Micro blood cards.
Figure 15B:
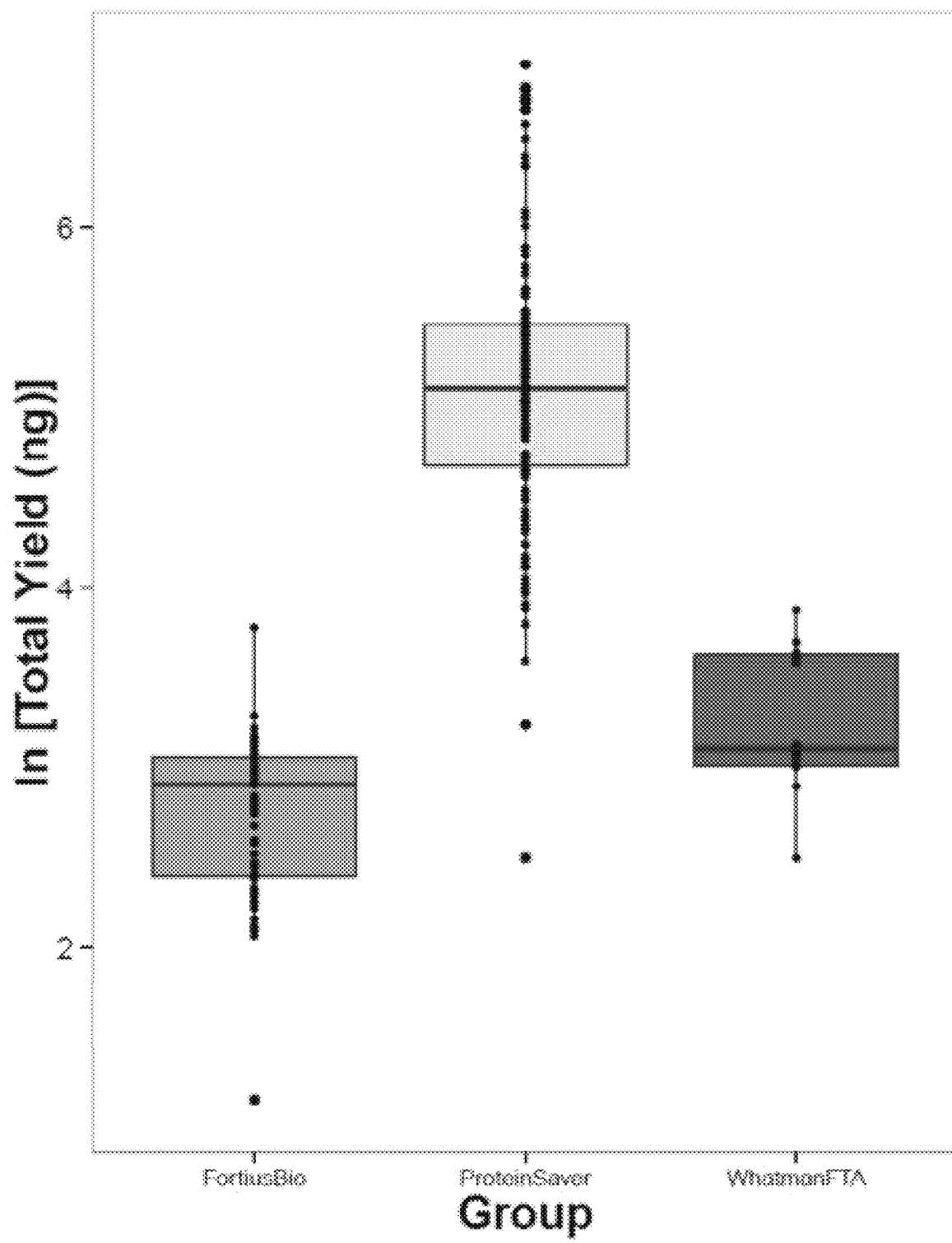
FIG. 15B depicts box plots with the same experimental data as that presented in FIG. 15A except the values are shown on a log scale.

The inventors also compared the quality and quantity of the RNAs obtained using the QIAAMP® and EXORNEASY® kits, as shown in FIGS. 9 and 10 and Table 3. Using a dried blood spot isolated from a sample collection apparatus and processed using the above-described protocols, the investigators were able to isolate acceptable quality RNAs (FIGS. 9 and 10) and of a sufficient concentration (Table 3). The standard curve associated with Table 3 is shown in FIG. 3.

Figure 4:
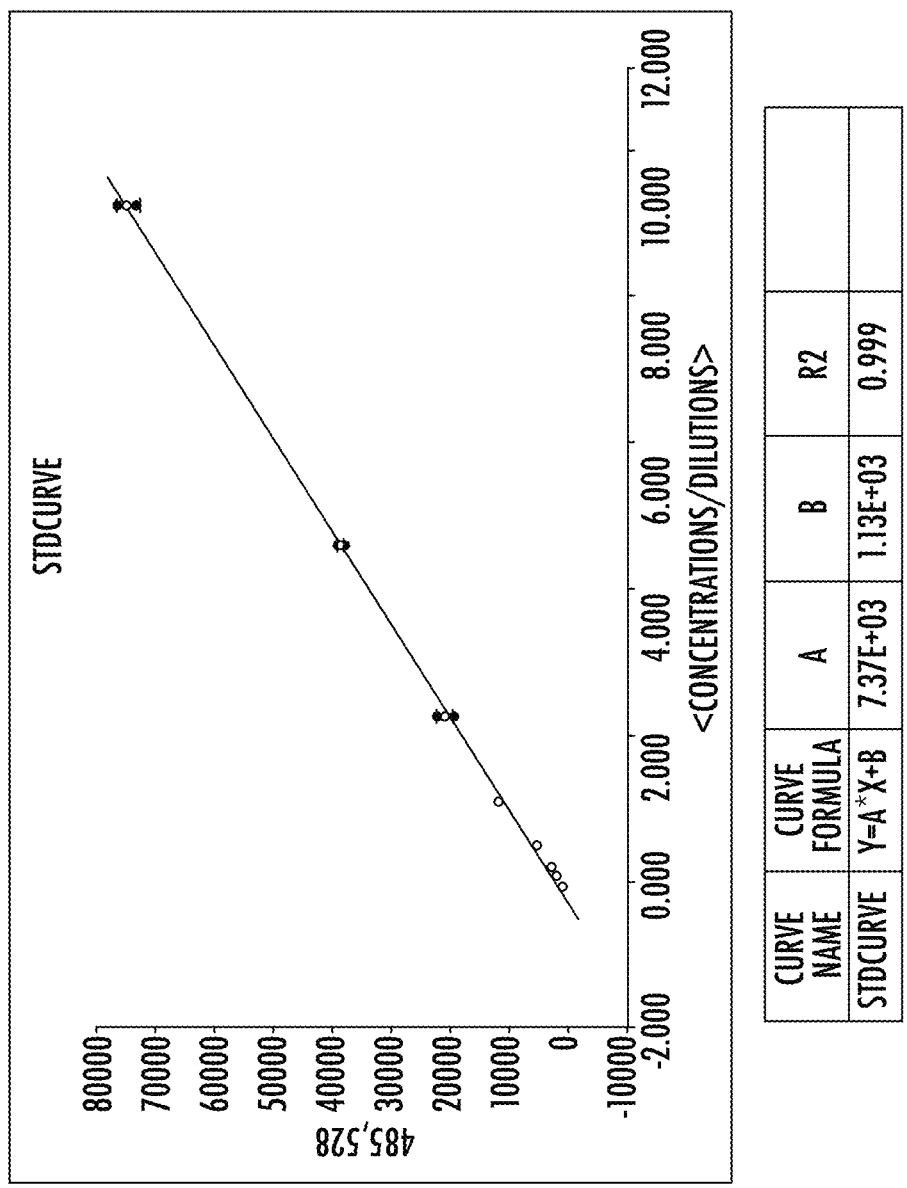
FIG. 4 depicts the standard curve used to calculate the RNA total yields in Table 4.
Figure 5:
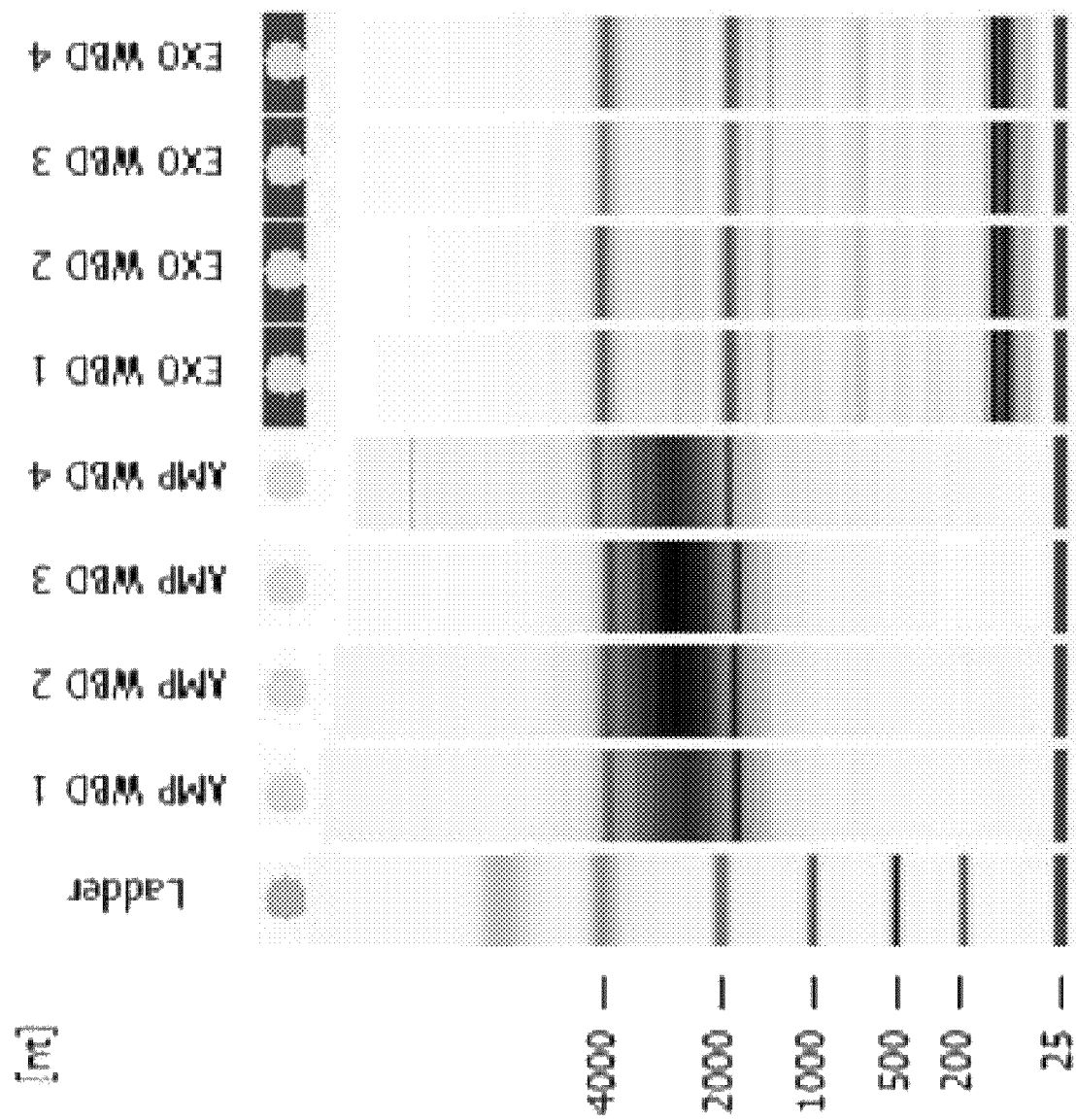
FIG. 5 depicts an assessment of the quality of RNA preparations from drops of wet whole blood by capillary electrophoresis.
Figure 6:
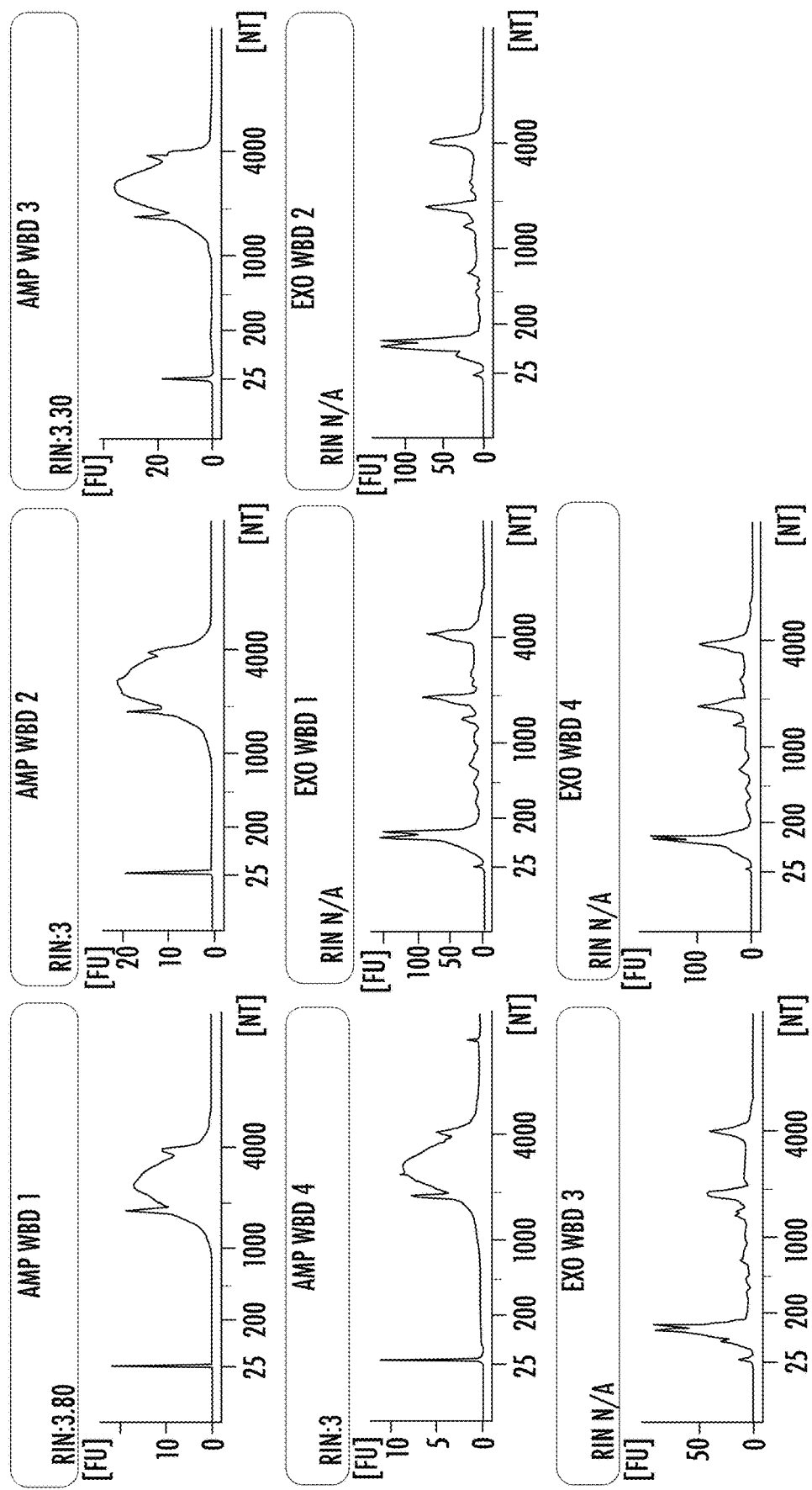
FIG. 6 depicts an analysis of the integrity of RNA preparations from drops of wet whole blood performed on an Agilent Bioanalyzer. The amount of RNA is depicted in fluorescence units (FU) for RNA molecules ranging in size from <25 nt to >4,000 nt.
Figure 7:
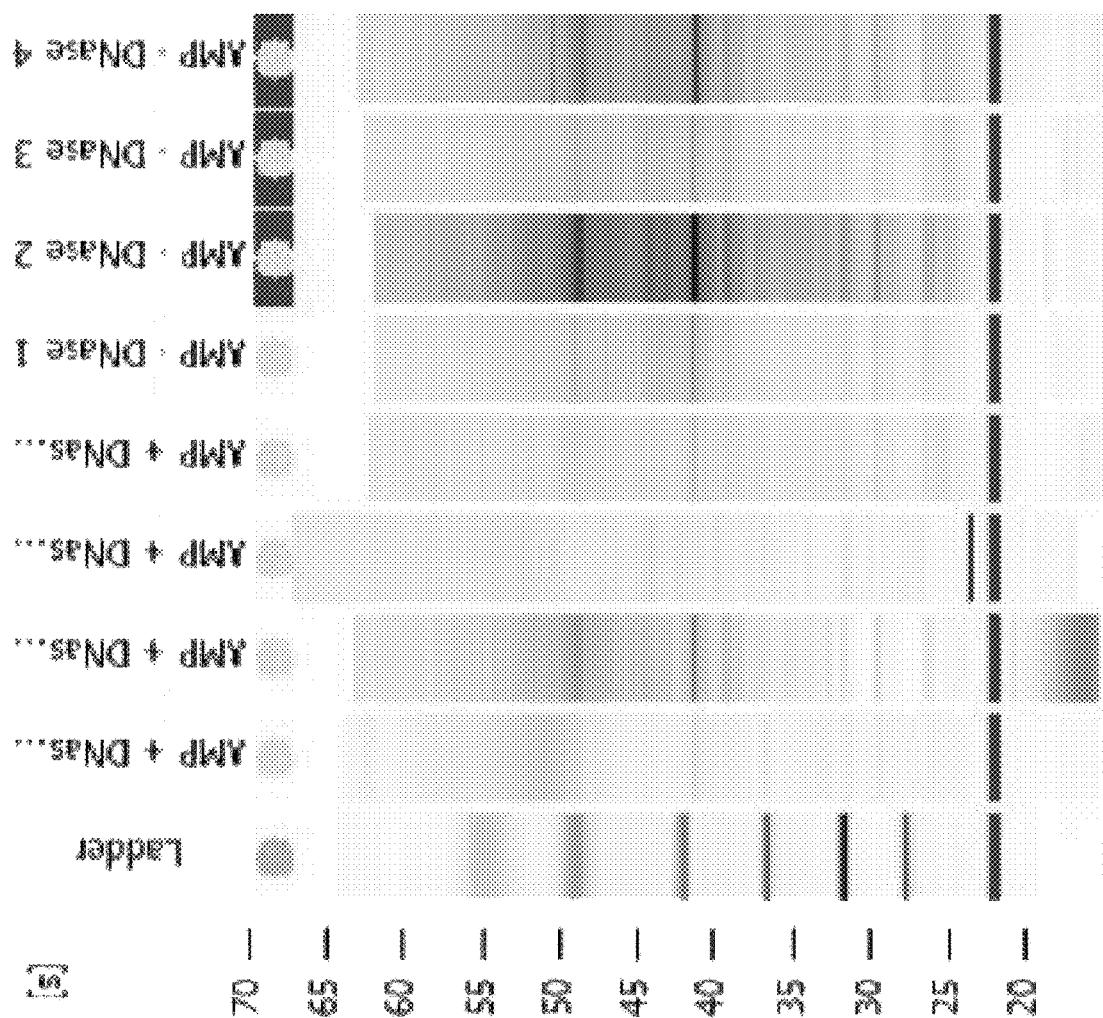
FIG. 7 depicts an assessment of the quality of RNA preparations from dried blood spots previously dried on a sample collection apparatus by capillary electrophoresis.
Figure 8:
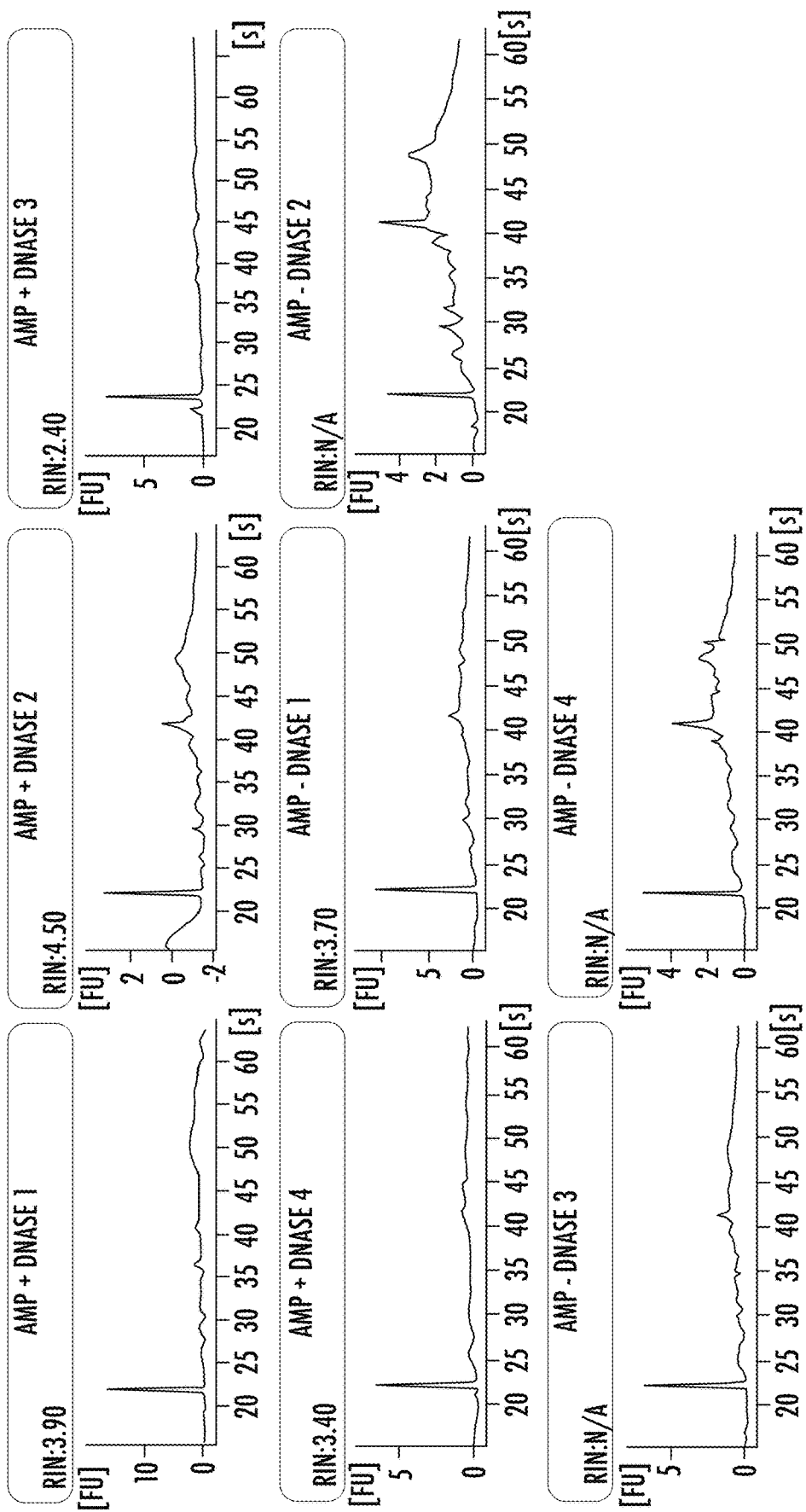
FIG. 8 depicts an analysis of the integrity of RNA preparations from dried blood spots previously dried on a sample collection apparatus performed on an Agilent Bioanalyzer. The amount of RNA is depicted in FU for RNA molecules ranging in size from <25 nt to >4,000 nt.

Finally, as illustrated in FIGS. 11-14 and Table 4, the inventors also conducted an investigation of the feasibility of collecting many samples from a subject who has been exercising. Using a dried blood spots isolated from one or more sample collection apparatuses and processed using the above-described protocols, the investigators were able to isolate acceptable quality RNAs (FIGS. 11-14) and of a sufficient concentration (Table 4). The standard curve associated with Table 4 is shown in FIG. 4.

TABLE 1

| Well ID | Name Well | Conc/Dil | 485,528 | [Concentration] | Count | Mean | Std Dev | CV (%) | Total Volume (ul) | Total Yield |
|---|---|---|---|---|---|---|---|---|---|---|
| AMP | A1 | | 11112 | 1.476 | 3 | 1.484 | 0.032 | 2.125 | 30 | 44.52 |
| WBD 1 | B1 | | 10969 | 1.457 | | | | | | |
| | C1 | | 11426 | 1.519 | | | | | | |
| AMP | A2 | | 13817 | 1.841 | 3 | 1.868 | 0.051 | 2.723 | 30 | 56.04 |
| WBD 2 | B2 | | 13777 | 1.836 | | | | | | |
| | C2 | | 14449 | 1.927 | | | | | | |
| AMP | A3 | | 21277 | 2.848 | 3 | 2.803 | 0.098 | 3.509 | 30 | 84.09 |
| WBD 3 | B3 | | 20108 | 2.69 | | | | | | |
| | C3 | | 21447 | 2.871 | | | | | | |
| AMP | A4 | | 11637 | 1.547 | 3 | 1.493 | 0.049 | 3.285 | 30 | 44.79 |
| WBD 4 | B4 | | 11134 | 1.479 | | | | | | |
| | C4 | | 10931 | 1.452 | | | | | | |
| EXO | A5 | | 60185 | 8.098 | 3 | 7.847 | 0.235 | 3 | 30 | 235.41 |
| WBD 1 | B5 | | 56725 | 7.631 | | | | | | |
| | C5 | | 58067 | 7.812 | | | | | | |
| EXO | A6 | | 49805 | 6.697 | 3 | 6.55 | 0.149 | 2.268 | 30 | 196.5 |
| WBD 2 | B6 | | 48730 | 6.552 | | | | | | |
| | C6 | | 47603 | 6.4 | | | | | | |
| EXO | A7 | | 31340 | 4.206 | 3 | 4.23 | 0.039 | 0.933 | 30 | 126.9 |
| WBD 3 | B7 | | 31857 | 4.275 | | | | | | |
| | C7 | | 31362 | 4.209 | | | | | | |
| EXO | A8 | | 63197 | 8.504 | 3 | 8.483 | 0.216 | 2.543 | 30 | 254.49 |
| WBD 4 | B8 | | 61366 | 8.257 | | | | | | |
| | C8 | | 64552 | 8.687 | | | | | | |
| STD1 | H10 | 10 | 75678 | 10.188 | 3 | 10.113 | 0.072 | 0.715 | | |
| | H11 | 10 | 74608 | 10.044 | | | | | | |
| | H12 | 10 | 75081 | 10.107 | | | | | | |

TABLE 1-continued

| Well ID | Name | Well | Conc/Dil | 485,528 | [Concentration] | Count | Mean | Std Dev | CV (%) | Total Volume (ul) | Total Yield |
|---|---|---|---|---|---|---|---|---|---|---|---|
| STD2 | | H7 | 5 | 35661 | 4.789 | 3 | 4.859 | 0.154 | 3.18 | | |
| | | H8 | 5 | 35384 | 4.751 | | | | | | |
| | | H9 | 5 | 37491 | 5.036 | | | | | | |
| STD3 | | H4 | 2.5 | 17947 | 2.399 | 3 | 2.461 | 0.059 | 2.391 | | |
| | | H5 | 2.5 | 18462 | 2.468 | | | | | | |
| | | H6 | 2.5 | 18814 | 2.516 | | | | | | |
| STD4 | | H1 | 1.25 | 3485 | 0.447 | 3 | 0.931 | 0.42 | 45.153 | | |
| | | H2 | 1.25 | 8608 | 1.139 | | | | | | |
| | | H3 | 1.25 | 9120 | 1.208 | | | | | | |
| STD5 | | G10 | 0.625 | 4911 | 0.64 | 3 | 0.696 | 0.06 | 8.655 | | |
| | | G11 | 0.625 | 5274 | 0.689 | | | | | | |
| | | G12 | 0.625 | 5799 | 0.76 | | | | | | |
| STD6 | | G7 | 0.3125 | 3323 | 0.425 | 3 | 0.36 | 0.057 | 15.764 | | |
| | | G8 | 0.3125 | 2554 | 0.322 | | | | | | |
| | | G9 | 0.3125 | 2642 | 0.334 | | | | | | |
| STD7 | | G4 | 0.15625 | 2147 | 0.267 | 3 | 0.247 | 0.019 | 7.727 | | |
| | | G5 | 0.15625 | 1981 | 0.244 | | | | | | |
| | | G6 | 0.15625 | 1866 | 0.229 | | | | | | |
| STD8 | | G1 | 0 | 1487 | 0.178 | 3 | 0.177 | 0.006 | 3.504 | | |
| | | G2 | 0 | 1529 | 0.183 | | | | | | |
| | | G3 | 0 | 1437 | 0.171 | | | | | | |

TABLE 2

| Well ID | Name | Well | Conc/Dil | 485,528 | [Concentration] | Count | Mean | Std Dev | CV (%) | Total Volume (ul) | Total Yield |
|---|---|---|---|---|---|---|---|---|---|---|---|
| 1 + AMP - DNase | with DNAase | A1 | | 3754 | 0.698 | 3 | 0.685 | 0.012 | 1.715 | 30 | 20.55 |
| | | B1 | | 3578 | 0.674 | | | | | | |
| | | C1 | | 3655 | 0.684 | | | | | | |
| 2 + AMP - DNase | | A2 | | 3510 | 0.665 | 3 | 0.668 | 0.01 | 1.549 | 30 | 20.04 |
| | | B2 | | 3617 | 0.679 | | | | | | |
| | | C2 | | 3466 | 0.659 | | | | | | |
| 3 + AMP - DNase | | A3 | | 2391 | 0.516 | 3 | 0.506 | 0.01 | 1.892 | 30 | 15.18 |
| | | B3 | | 2301 | 0.504 | | | | | | |
| | | C3 | | 2249 | 0.497 | | | | | | |
| 4 + AMP - DNase | | A4 | | 2836 | 0.575 | 3 | 0.569 | 0.013 | 2.355 | 30 | 17.07 |
| | | B4 | | 2853 | 0.578 | | | | | | |
| | | C4 | | 2671 | 0.553 | | | | | | |
| 1 − AMP - DNase | without DNAse | A5 | | 4560 | 0.805 | 3 | 0.795 | 0.009 | 1.15 | 30 | 23.85 |
| | | B5 | | 4471 | 0.793 | | | | | | |
| | | C5 | | 4425 | 0.787 | | | | | | |
| 2 − AMP - DNase | | A6 | | 6412 | 1.052 | 3 | 1.008 | 0.044 | 4.336 | 30 | 30.24 |
| | | B6 | | 5756 | 0.964 | | | | | | |
| | | C6 | | 6079 | 1.007 | | | | | | |
| 3 − AMP - DNase | | A7 | | 3870 | 0.713 | 3 | 0.695 | 0.016 | 2.234 | 30 | 20.85 |
| | | B7 | | 3676 | 0.687 | | | | | | |
| | | C7 | | 3661 | 0.685 | | | | | | |
| 4 − AMP - DNase | | A8 | | 4394 | 0.783 | 3 | 0.77 | 0.011 | 1.384 | 30 | 23.1 |
| | | B8 | | 4252 | 0.764 | | | | | | |
| | | C8 | | 4259 | 0.765 | | | | | | |
| STD1 | | H10 | 10 | 76090 | 10.333 | 2 | 9.914 | 0.592 | 5.971 | | |
| | | H11 | 10 | 78987 | >10.500 | | | | | | |
| | | H12 | 10 | 69805 | 9.496 | | | | | | |
| STD2 | | H7 | 5 | 34320 | 4.769 | 3 | 4.897 | 0.198 | 4.048 | | |
| | | H8 | 5 | 34523 | 4.796 | | | | | | |
| | | H9 | 5 | 36993 | 5.125 | | | | | | |
| STD3 | | H4 | 2.5 | 14887 | 2.18 | 3 | 2.179 | 0.076 | 3.506 | | |
| | | H5 | 2.5 | 14301 | 2.102 | | | | | | |
| | | H6 | 2.5 | 15448 | 2.255 | | | | | | |
| STD4 | | H1 | 1.25 | 1595 | 0.41 | 3 | 0.815 | 0.351 | 43.047 | | |
| | | H2 | 1.25 | 6086 | 1.008 | | | | | | |
| | | H3 | 1.25 | 6223 | 1.026 | | | | | | |
| STD5 | | G10 | 0.625 | 2658 | 0.552 | 3 | 0.561 | 0.015 | 2.69 | | |
| | | G11 | 0.625 | 2668 | 0.553 | | | | | | |
| | | G12 | 0.625 | 2859 | 0.578 | | | | | | |
| STD6 | | G7 | 0.3125 | 2483 | 0.528 | 3 | 0.445 | 0.073 | 16.452 | | |
| | | G8 | 0.3125 | 1458 | 0.392 | | | | | | |
| | | G9 | 0.3125 | 1628 | 0.414 | | | | | | |

TABLE 2-continued

| Well ID | Name | Well | Conc/Dil | 485,528 | [Concentration] | Count | Mean | Std Dev | CV (%) | Total Volume (ul) | Total Yield |
|---|---|---|---|---|---|---|---|---|---|---|---|
| STD7 | | G4 | 0.15625 | 1463 | 0.392 | 3 | 0.384 | 0.014 | 3.591 | | |
| | | G5 | 0.15625 | 1464 | 0.392 | | | | | | |
| | | G6 | 0.15625 | 1284 | 0.369 | | | | | | |
| STD8 | | G1 | 0 | 1431 | 0.388 | 3 | 0.38 | 0.008 | 2.034 | | |
| | | G2 | 0 | 1369 | 0.38 | | | | | | |
| | | G3 | 0 | 1315 | 0.373 | | | | | | |

TABLE 3

| Well ID | Name | Well | Conc/Dil | 485,528 | [Concentration] | Count | Mean | Std Dev | CV (%) | Total Volume (ul) | Total Yield (ng) |
|---|---|---|---|---|---|---|---|---|---|---|---|
| AMP 1 | | A1 | | 3016 | 0.441 | 3 | 0.449 | 0.013 | 2.813 | 30 | 13.47 |
| | | B1 | | 3028 | 0.442 | | | | | | |
| | | C1 | | 3187 | 0.463 | | | | | | |
| AMP 2 | | A2 | | 3979 | 0.568 | 3 | 0.603 | 0.035 | 5.725 | 30 | 18.09 |
| | | B2 | | 4249 | 0.604 | | | | | | |
| | | C2 | | 4501 | 0.637 | | | | | | |
| AMP 3 | | A3 | | 3478 | 0.502 | 3 | 0.515 | 0.016 | 3.136 | 30 | 15.45 |
| | | B3 | | 3545 | 0.511 | | | | | | |
| | | C3 | | 3715 | 0.533 | | | | | | |
| AMP 4 | | A4 | | 3400 | 0.491 | 3 | 0.501 | 0.032 | 6.444 | 30 | 15.03 |
| | | B4 | | 3267 | 0.474 | | | | | | |
| | | C4 | | 3740 | 0.536 | | | | | | |
| EXO 1 | | A5 | | 2094 | 0.319 | 3 | 0.326 | 0.011 | 3.308 | 30 | 9.78 |
| | | B5 | | 2111 | 0.321 | | | | | | |
| | | C5 | | 2243 | 0.338 | | | | | | |
| EXO 2 | | A6 | | 2288 | 0.344 | 3 | 0.342 | 0.005 | 1.392 | 30 | 10.26 |
| | | B6 | | 2230 | 0.337 | | | | | | |
| | | C6 | | 2296 | 0.345 | | | | | | |
| EXO 3 | | A7 | | 2626 | 0.389 | 3 | 0.394 | 0.018 | 4.655 | 30 | 11.82 |
| | | B7 | | 2551 | 0.379 | | | | | | |
| | | C7 | | 2820 | 0.415 | | | | | | |
| EXO 4 | | A8 | | 3300 | 0.478 | 3 | 0.482 | 0.008 | 1.703 | 30 | 14.46 |
| | | B8 | | 3396 | 0.491 | | | | | | |
| | | C8 | | 3280 | 0.476 | | | | | | |
| STD1 | | H10 | 10 | 72917 | 9.684 | 3 | 9.896 | 0.252 | 2.551 | | |
| | | H11 | 10 | 74010 | 9.828 | | | | | | |
| | | H12 | 10 | 76632 | 10.175 | | | | | | |
| STD2 | | H7 | 5 | 38571 | 5.142 | 3 | 5.281 | 0.225 | 4.255 | | |
| | | H8 | 5 | 38707 | 5.16 | | | | | | |
| | | H9 | 5 | 41580 | 5.54 | | | | | | |
| STD3 | | H4 | 2.5 | 18004 | 2.423 | 3 | 2.46 | 0.167 | 6.791 | | |
| | | H5 | 2.5 | 17188 | 2.315 | | | | | | |
| | | H6 | 2.5 | 19667 | 2.642 | | | | | | |
| STD4 | | H1 | 1.25 | 10277 | 1.401 | 3 | 1.176 | 0.194 | 16.53 | | |
| | | H2 | 1.25 | 7785 | 1.071 | | | | | | |
| | | H3 | 1.25 | 7678 | 1.057 | | | | | | |
| STD5 | | G10 | 0.625 | 2564 | 0.381 | 3 | 0.386 | 0.054 | 13.929 | | |
| | | G11 | 0.625 | 2212 | 0.334 | | | | | | |
| | | G12 | 0.625 | 3022 | 0.441 | | | | | | |
| STD6 | | G7 | 0.3125 | 1319 | 0.216 | 3 | 0.221 | 0.019 | 8.383 | | |
| | | G8 | 0.3125 | 1511 | 0.242 | | | | | | |
| | | G9 | 0.3125 | 1238 | 0.206 | | | | | | |
| STD7 | | G4 | 0.15625 | 1361 | 0.222 | 3 | 0.216 | 0.012 | 5.405 | | |
| | | G5 | 0.15625 | 1214 | 0.202 | | | | | | |
| | | G6 | 0.15625 | 1372 | 0.223 | | | | | | |
| STD8 | | G1 | 0 | 1262 | 0.209 | 3 | 0.208 | 0.007 | 3.557 | | |
| | | G2 | 0 | 1314 | 0.216 | | | | | | |
| | | G3 | 0 | 1202 | 0.201 | | | | | | |

TABLE 4

| Well ID | Name Well | Conc/Dil | 485,828 | [Concentration] | Count | Mean | Std Dev | CV (%) | Total Volume (ul) | Total Yield |
|---|---|---|---|---|---|---|---|---|---|---|
| 530 PRE | A1 | | 4315 | 0.432 | 3 | 0.435 | 0.004 | 0.957 | 30 | 13.05 |
| | B1 | | 4372 | 0.44 | | | | | | |
| | C1 | | 4324 | 0.433 | | | | | | |
| 930 PRE | A2 | | 6140 | 0.68 | 3 | 0.677 | 0.002 | 0.364 | 30 | 20.31 |
| | B2 | | 6105 | 0.675 | | | | | | |
| | C2 | | 6114 | 0.676 | | | | | | |
| 10 M | A3 | | 4798 | 0.497 | 3 | 0.505 | 0.009 | 1.805 | 30 | 15.15 |
| | B3 | | 4930 | 0.515 | | | | | | |
| | C3 | | 4842 | 0.503 | | | | | | |
| 20 M | A4 | | 4185 | 0.414 | 3 | 0.423 | 0.017 | 3.976 | 30 | 12.69 |
| | B4 | | 4174 | 0.413 | | | | | | |
| | C4 | | 4394 | 0.443 | | | | | | |
| 30 M | A5 | | 4985 | 0.523 | 3 | 0.523 | 0.008 | 1.506 | 30 | 15.69 |
| | B5 | | 5043 | 0.531 | | | | | | |
| | C5 | | 4927 | 0.515 | | | | | | |
| 40 M | A6 | | 5257 | 0.56 | 3 | 0.52 | 0.035 | 6.66 | 30 | 15.6 |
| | B6 | | 4797 | 0.497 | | | | | | |
| | C6 | | 4836 | 0.503 | | | | | | |
| 50 M | A7 | | 3975 | 0.386 | 3 | 0.379 | 0.01 | 2.653 | 30 | 11.37 |
| | B7 | | 3838 | 0.367 | | | | | | |
| | C7 | | 3955 | 0.383 | | | | | | |
| 60 M | A8 | | 4235 | 0.421 | 3 | 0.386 | 0.043 | 11.189 | 30 | 11.58 |
| | B8 | | 4072 | 0.399 | | | | | | |
| | C8 | | 3621 | 0.338 | | | | | | |
| 1 HR POST | A9 | | 4630 | 0.475 | 3 | 0.47 | 0.023 | 4.84 | 30 | 14.1 |
| | B9 | | 4411 | 0.445 | | | | | | |
| | C9 | | 4740 | 0.49 | | | | | | |
| 2 HR POST | A10 | | 4045 | 0.395 | 3 | 0.379 | 0.016 | 4.103 | 30 | 11.37 |
| | B10 | | 3906 | 0.376 | | | | | | |
| | C10 | | 3818 | 0.364 | | | | | | |
| 3 HR POST | A11 | | 3707 | 0.349 | 3 | 0.381 | 0.028 | 7.362 | 30 | 11.43 |
| | B11 | | 4095 | 0.402 | | | | | | |
| | C11 | | 4025 | 0.393 | | | | | | |
| 4 HR POST | A12 | | 4221 | 0.419 | 3 | 0.414 | 0.01 | 2.481 | 30 | 12.42 |
| | B12 | | 4098 | 0.402 | | | | | | |
| | C12 | | 4236 | 0.421 | | | | | | |
| STD1 | H10 | 10 | 73297 | 9.796 | 3 | 9.932 | 0.251 | 2.526 | | |
| | H11 | 10 | 73170 | 9.779 | | | | | | |
| | H12 | 10 | 76433 | 10.222 | | | | | | |
| STD2 | H7 | 5 | 38293 | 5.044 | 3 | 5.031 | 0.086 | 1.711 | | |
| | H8 | 5 | 38777 | 5.11 | | | | | | |
| | H9 | 5 | 37520 | 4.939 | | | | | | |
| STD3 | H4 | 2.5 | 21911 | 2.821 | 3 | 2.659 | 0.182 | 6.842 | | |
| | H5 | 2.5 | 20973 | 2.693 | | | | | | |
| | H6 | 2.5 | 19268 | 2.462 | | | | | | |
| STD4 | H1 | 1.25 | 11571 | 1.417 | 3 | 1.425 | 0.015 | 1.061 | | |
| | H2 | 1.25 | 11558 | 1.415 | | | | | | |
| | H3 | 1.25 | 11757 | 1.442 | | | | | | |
| STD5 | G10 | 0.625 | 4825 | 0.501 | 3 | 0.537 | 0.037 | 6.824 | | |
| | G11 | 0.625 | 5084 | 0.536 | | | | | | |
| | G12 | 0.625 | 5365 | 0.574 | | | | | | |
| STD6 | G7 | 0.3125 | 2433 | 0.176 | 3 | 0.215 | 0.035 | 16.155 | | |
| | G8 | 0.3125 | 2798 | 0.226 | | | | | | |
| | G9 | 0.3125 | 2927 | 0.243 | | | | | | |
| STD7 | G4 | 0.15625 | 1809 | 0.092 | 3 | 0.092 | 0.001 | 0.592 | | |
| | G5 | 0.15625 | 1813 | 0.092 | | | | | | |
| | G6 | 0.15625 | 1805 | 0.091 | | | | | | |
| STD8 | G1 | 0 | 788 | <0.000 | 0 | — | — | — | | |
| | G2 | 0 | 809 | <0.000 | | | | | | |
| | G3 | 0 | 752 | <0.000 | | | | | | |

Example 2. Novel Informatics Approach for the Analysis of Dried Blood Spot RNA-Seq Initial steps in the analysis of dried blood spot (DBS) RNA-seq are similar to standard RNA-seq analysis pipelines. The raw sequencing reads must be trimmed of adapters (Cutadapt, AlienTrimmer), aligned to a reference (STAR, Tophat), and quantitated (FeatureCounts, htseq-count) to generate numerical estimates of each gene's expression, or "counts". The principle issue is recognizing variance in these counts due to technical reasons that do not represent biological significance.

In standard (non-DBS) RNA-seq experiments, this is addressed with a simple expression cutoff (i.e., any gene detected with >n counts usually exhibits low variance among replicates). This is not suitable for DBS samples, as the process of drying imparts a non-uniform effect across transcripts of variable length, presumably due to their biochemical structure and stability. To summarize, the process of drying RNA results in "messy" or "noisy" data.

To control for this, the stability of different dried transcripts is surveyed by sequencing technical replicates and calculating the coefficient of variance for each transcript on different collections mediums (i.e., the "CV DBS"). This gives us an idea of each transcript's stability during drying and potential accuracy as a biomarker when collected on a particular paper. The investigators utilize this data in a two-step filtering approach.

First, the investigators have created a database of transcript coefficients of variance by using standard (non-DBS) RNA-seq to survey a dozen technical replicates of control HEK RNA (i.e., a database of "CV Standard" values). Because they are technical replicates (biologically identical), this information allows us to filter human transcripts exhibiting high variance due solely to technical reasons.

Secondly, the investigators have created highly specific coefficient of variance databases for each sample type and preparation method (i.e., databases of "CV DBS" values). This information can be used to filter project-specific technical variance and identify good transcriptional biomarkers. Representative biomarkers with good potential (i.e., "CV DBS" values and "CV Standard" values that are relatively low) and with poor potential (i.e., "CV DBS" values and/or "CV Standard" values that are relatively high) are shown in Table 5.

This two-step CV filtering approach represents a novel and necessary step in the analysis of DBS RNA-seq analysis. Furthermore, as the investigators have observed large amounts of variance in several highly detected transcripts from standard RNA-seq, our CV filter approach may also be useful for typical RNA-seq sample types and techniques.

Example 4. Identification of Biomarkers of Aerobic Exercise

Figure 16:
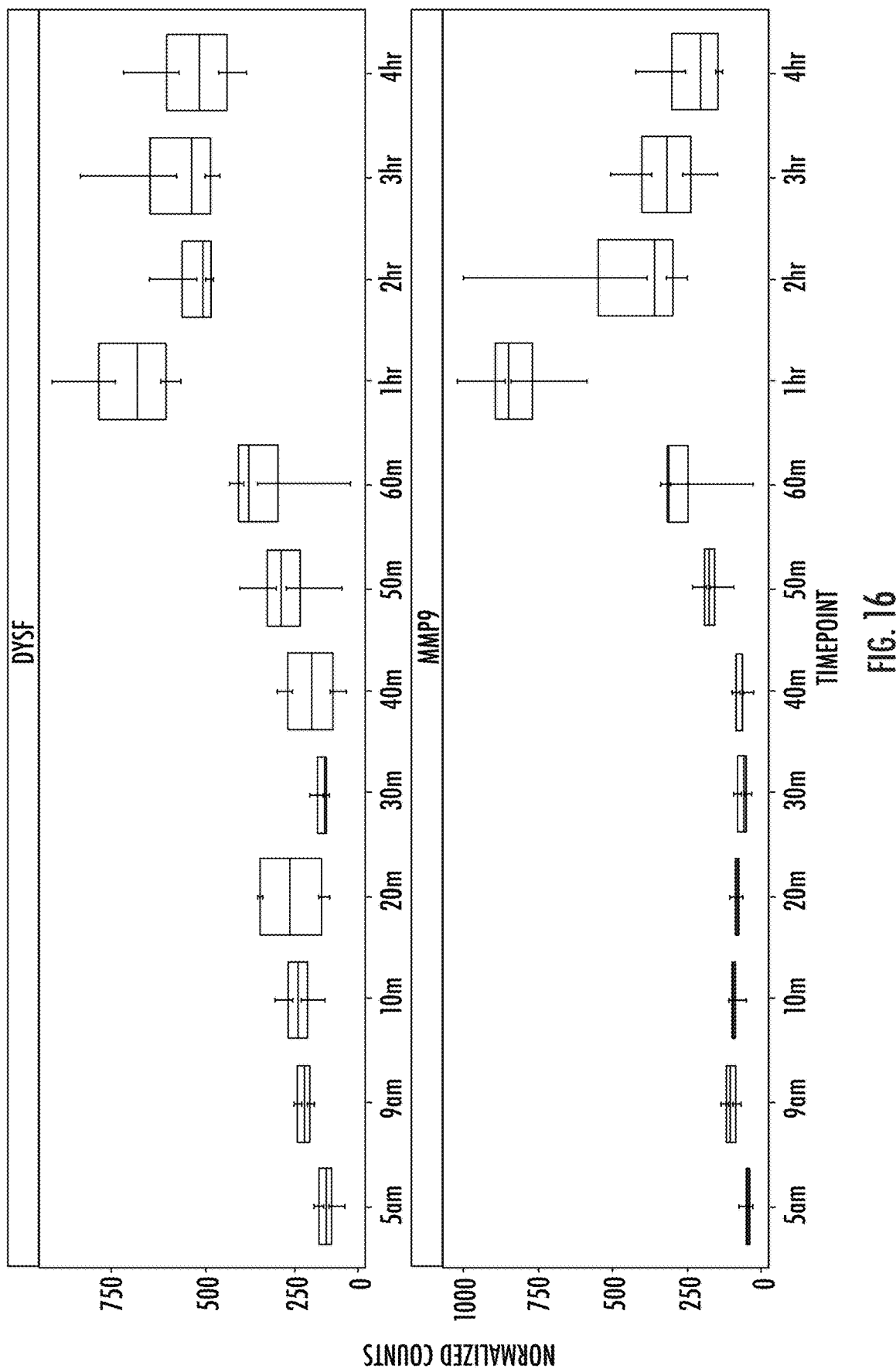
FIG. 16 depicts normalized counts of DYSF (dysferlin) and MMP9 (matrix metallopeptidase 9) analyzed in dried blood samples from a human subject at 5 am and 9 am (pre-exercise), at ten minute intervals during exercise, and hourly post-exercise.

Potential biomarkers of aerobic exercise (cycling) were identified with the DBS technology disclosed herein. Samples were collected at 5 am and 9 am (pre-exercise), at ten minute intervals during exercise, and hourly post-exercise. DYSF (dysferlin; Ensembl:ENSG00000135636; NCBI Gene ID: 8291) and MMP9 (matrix metallopeptidase 9; Ensembl:ENSG00000100985; NCBI Gene ID: 4318) exhibited increased expression after an hour of cycling, peaked one hour post-exercise, and gradually decreased afterwards (see FIG. 16).

Figure 17:
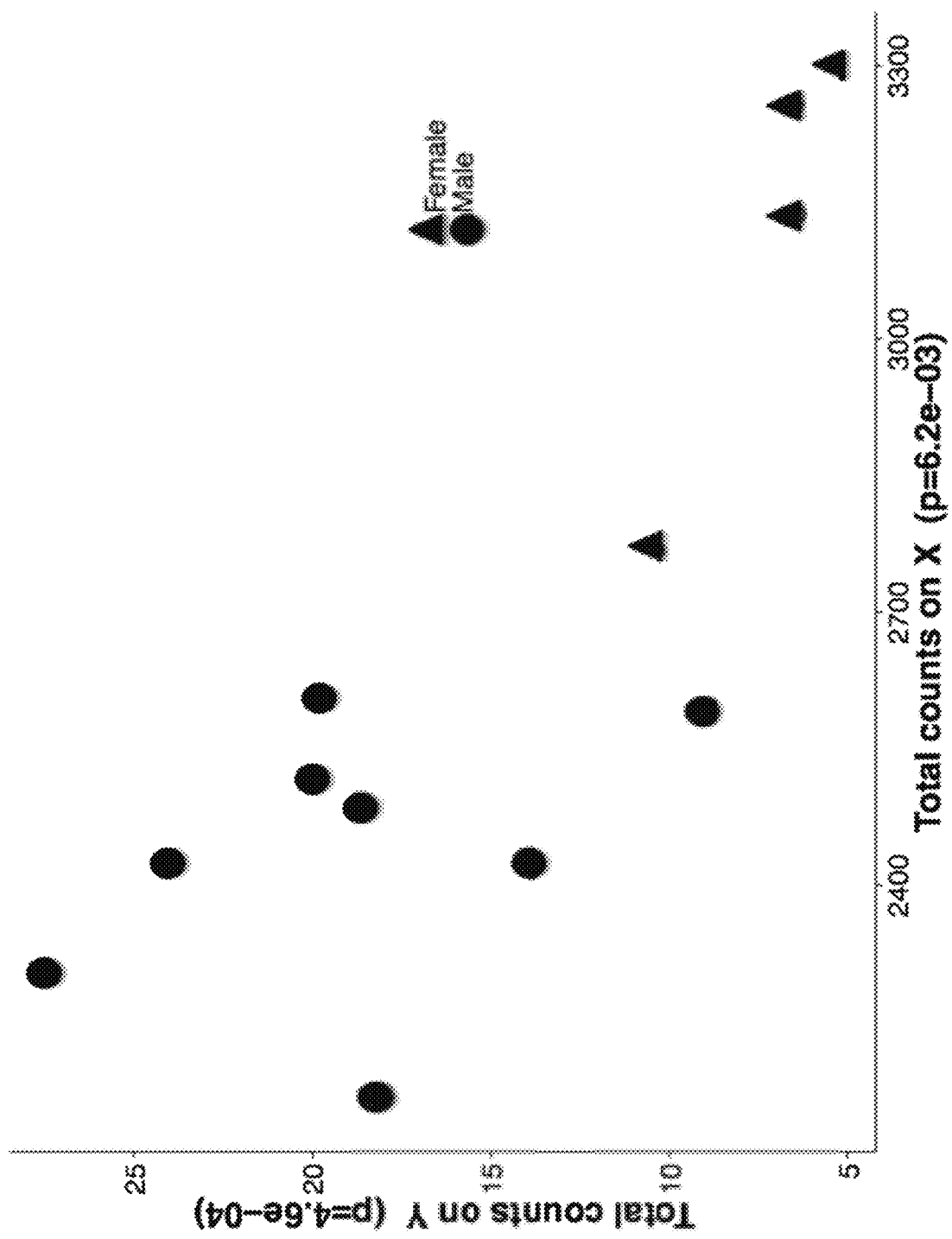
FIG. 17 depicts analysis of cell-free RNA in maternal plasma and measurement of the expression of biomarkers specific to the X chromosome or to the Y chromosome to determine fetal sex.

Example 5. Fetal Sex Determination with DBS Analysis of Cell-Free RNA in Maternal Plasma Fetal sex may be determined with the DBS methods disclosed herein. In the plot presented in FIG. 17, cell-free RNA in maternal plasma was analyzed for the expression of biomarkers specific to the X chromosome or to the Y chromosome. The data in the plot demonstrate a clear differentiation between male and female fetuses when using cell-free RNA-seq of maternal plasma. Samples with high counts of RNA specific to the Y chromosome identify male fetuses. The DBS methods disclosed herein offer a simpler,

TABLE 5

| EnsemblID | Gene | CV DBS | CV Standard | Biomarker Potential |
|---|---|---|---|---|
| ENSG00000183508 | FAM46C | 0.060717822 | 0.087871342 | good |
| ENSG00000114166 | KAT2B | 0.081479834 | 0.085560905 | good |
| ENSG00000122026 | RPL21 | 0.081957896 | 0.07062178 | good |
| ENSG00000136732 | GYPC | 0.082907156 | 0.144888107 | good |
| ENSG00000140264 | SERF2 | 0.092065358 | 0.147809395 | good |
| ENSG00000006468 | ETV1 | 3.464101615 | 0.09928696 | poor |
| ENSG00000125997 | BPIFB9P | 3.464101615 | 0.466427796 | poor |
| ENSG00000264573 | RN7SL15P | 3.464101615 | 0.334895213 | poor |
| ENSG00000269959 | SPACA6P-AS | 3.464101615 | 0.170486395 | poor |
| ENSG00000059573 | ALDH18A1 | 3.464101615 | 0.010980315 | poor |

Example 3. Evaluation of Performance of Several Sample Collection Apparatuses Several sample collection apparatuses were evaluated for their efficiency in stabilizing RNA in dried blood samples. FORTIUSBIO® RNASOUND™ blood sampling cards contain a proprietary solution that lyses cells and releases RNA that is stabilized on the card for at least one week at room temperature. WHATMAN® FTA® non-indicating Elute Micro blood cards contain a lysis buffer consisting of EDTA, Tris, sodium dodecyl sulfate (SDS), and uric acid to lyse and stabilize DNA in the sample. WHATMAN® 903 Protein Saver cards are an untreated cellulose paper for blood sampling. Multiple, equivalent dried blood samples were collected with each of the three cards and the RNA in the samples was analyzed as described in Example 1.

Of the three cards tested, the WHATMAN® 903 Protein Saver cards out-performed the other cards in RNA recovery, gene expression profiling, and reproducibility. Surprisingly, the card without any added material designed to stabilize nucleic acid (i.e., untreated cellulose paper) performed the best.

more cost-effective, and safer means of determining fetal sex than do other assays currently available.

Example 6. Identification of Biomarkers Correlating with Onset of Migraine

Figure 18:
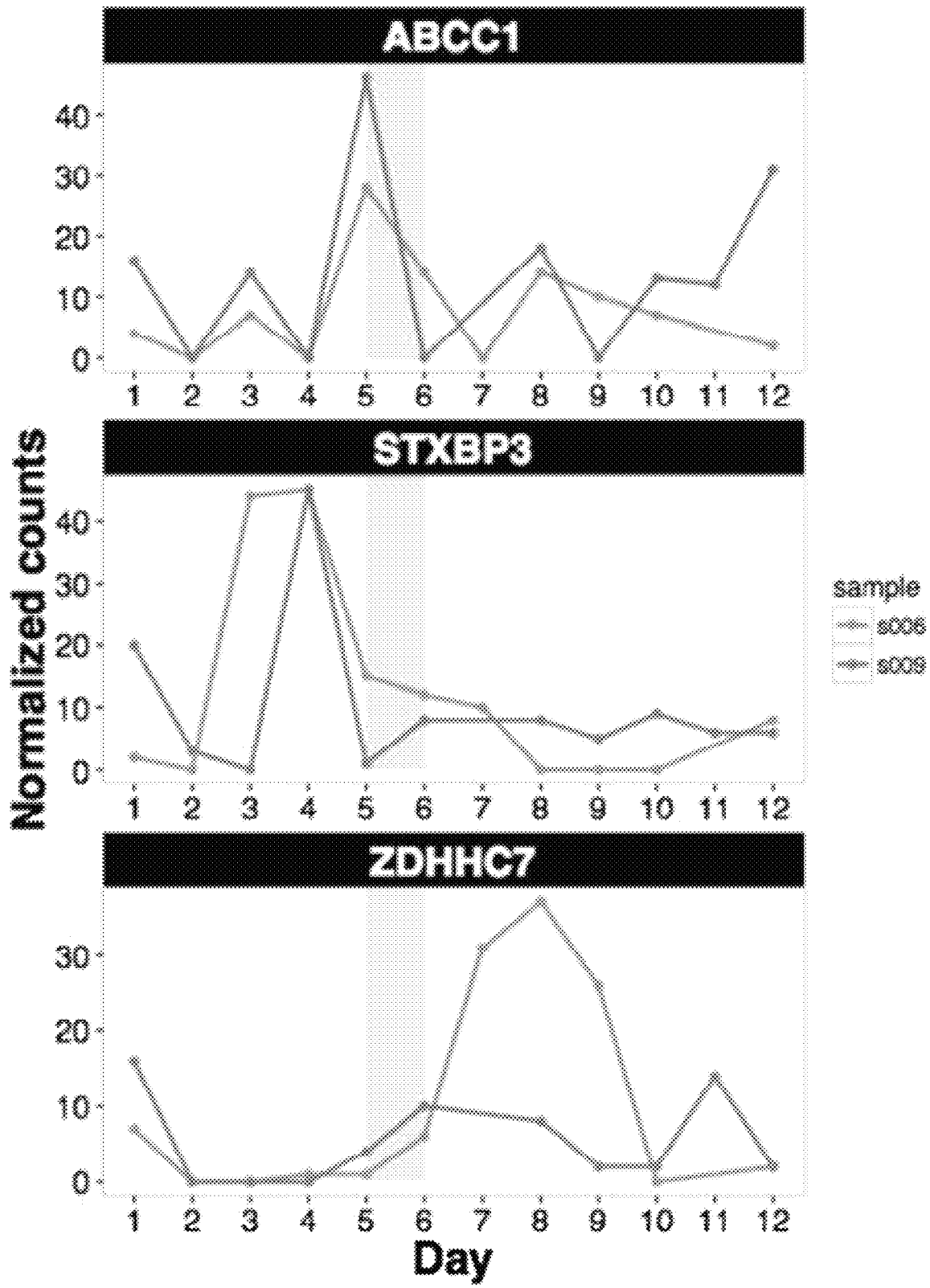
FIG. 18 depicts two time series of dried blood sample collection and analysis conducted with a human subject where samples were drawn before, during, and after onset of a migraine. Onset of migraine is indicated in the charts by the vertical gray bar between days 5 and 6.

Two different time series of dried blood sample collection and analysis were conducted with a human subject where samples were drawn before, during, and after onset of a migraine. Three biomarkers were identified with the DBS method that correlate with the onset of migraine. Each exhibits a different expression pattern which may be indicative of roles in transcriptional pathways (see FIG. 18). The biomarkers are:
 ABCC1 (ATP binding cassette subfamily C member 1; Ensembl:ENSG00000103222; NCBI Gene ID: 4363);
 STXBP3 (syntaxin binding protein 3; Ensembl: ENSG00000116266; NCBI Gene ID: 6814); and
 ZDHHC7 (zinc finger DHHC-type containing 7; Ensembl:ENSG00000153786; NCBI Gene ID: 55625).

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A method of predicting onset of a migraine in a human subject, the method comprising the steps of:
    obtaining a set of samples of biofluid from the human subject collected over time intervals and stored on sample collection apparatuses, wherein the biofluid is blood and the sample collection apparatus comprises a cellulose paper on which the biofluid is placed to dry, and the cellulose paper has not been treated with any chemical stabilizers of nucleic acids;
    extracting nucleic acids from the set of samples, wherein the nucleic acids are RNA;
    sequencing the extracted nucleic acids to generate sequence data, wherein the RNA is sequenced with RNA-seq; and
    analyzing the sequence data to identify increases in syntaxin binding protein 3 (STXBP3), wherein an at least five times increase in expression of STXBP3 compared with a sample collected at an earlier time interval indicates onset of a migraine in the human subject.

2. The method of claim 1, wherein the RNA is extracellular RNA.

3. The method of claim 1, wherein the sample is obtained from the subject through a non-invasive methodology.

4. The method of claim 3, wherein the non-invasive methodology is a finger prick.

5. The method of claim 1, wherein the increase in expression is an increase of at least 20 times in a 12-hour period.

6. The method of claim 1, wherein the time intervals are 4 hours, 6 hours, 12 hours or 24 hours.

7. The method of claim 1, wherein the set of samples is a set of single drops of blood allowed to dry on the sample collection apparatuses.

8. The method of claim 1, further comprising treating the subject for migraine when an at least five times increase in expression of STXBP3 compared with a sample collected at an earlier time interval occurs, wherein treating the migraine comprises administering to the subject an effective amount of a non-steroidal anti-inflammatory drug (NSAID), a triptan, an ergotamine, metoclopramide, lidocaine or a combination thereof.

9. A method of predicting onset of a migraine in a human subject, the method comprising the steps of:
    obtaining a set of samples of biofluid from the subject collected over time intervals and stored on sample collection apparatuses, wherein the biofluid is blood;
    extracting nucleic acids from the set of samples, wherein the nucleic acids are RNA;
    sequencing the extracted nucleic acids to generate sequence data, wherein the RNA is sequenced with RNA-Seq;
    analyzing the sequence data to identify changes in gene expression syntaxin binding protein 3 (STXBP3), wherein an at least five times increase in expression of STXBP3 compared to an earlier sample indicates onset of a migraine in the subject; and
    treating the human subject for migraine when an at least five times increase in expression of STXBP3 compared with a sample collected at an earlier time interval occurs, wherein treating the migraine comprises administering to the subject an effective amount of a non-steroidal anti-inflammatory drug (NSAID), a triptan, an ergotamine, metoclopramide, lidocaine or a combination thereof;
    wherein the sample is stored on a sample collection apparatus, the sample collection apparatus comprises cellulose paper on which the biofluid is placed to dry, and the cellulose paper has not been treated with any chemical stabilizers of nucleic acids.

10. The method of claim 9, wherein the sample is obtained from the subject through a non-invasive methodology.

11. The method of claim 9, wherein an increase in expression is an increase of at least 20 times in a 12-hour period.

12. The method of claim 9, wherein the time intervals are 4 hours, 6 hours, 12 hours or 24 hours.

13. The method of claim 9, wherein the set of samples is a set of single drops of blood allowed to dry on the sample collection apparatuses.

14. The method of claim 9, wherein the RNA is extracellular RNA.

15. The method of claim 1, wherein analyzing the sequence data also identifies increases in ATP binding cassette subfamily C member 1 (ABCC1).

16. The method of claim 9, wherein analyzing the sequence data also identifies increases in ATP binding cassette subfamily C member 1 (ABCC1).

17. The method of claim 8, wherein treating the subject for a migraine occurs after an at least five times increase in expression of STXBP3 compared with a sample collected at an earlier time interval is detected and before the onset of the migraine occurs.

18. The method of claim 9, wherein treating the subject for a migraine occurs after an at least five times increase in expression of STXBP3 compared with a sample collected at an earlier time interval is detected and before the onset of the migraine occurs.

* * * * *